United States Patent
Newton et al.

(10) Patent No.: US 9,637,470 B2
(45) Date of Patent: May 2, 2017

(54) TREATMENT FOR SUBSTANCE USE DISORDERS AND STRESS DISORDERS

(71) Applicant: Baylor College of Medicine, Houston, TX (US)

(72) Inventors: Thomas F. Newton, Houston, TX (US); Colin N. Haile, Blieberville, TX (US)

(*) Notice: Subject to any disclaimer, the term of this patent is extended or adjusted under 35 U.S.C. 154(b) by 74 days.

(21) Appl. No.: 14/187,269

(22) Filed: Feb. 22, 2014

(65) Prior Publication Data
US 2014/0249183 A1 Sep. 4, 2014

Related U.S. Application Data

(60) Provisional application No. 61/767,886, filed on Feb. 22, 2013.

(51) Int. Cl.
*C07D 401/06* (2006.01)
*C07D 409/14* (2006.01)
*A61K 31/454* (2006.01)

(52) U.S. Cl.
CPC ......... *C07D 401/06* (2013.01); *C07D 409/14* (2013.01); *A61K 31/454* (2013.01)

(58) Field of Classification Search
CPC .. C07D 401/06; C07D 409/14; C07D 403/06; C07D 403/14; A61K 31/454
See application file for complete search history.

(56) References Cited

U.S. PATENT DOCUMENTS

| | | | |
|---|---|---|---|
| 7,247,643 B2 | 7/2007 | Peters et al. | |
| 8,513,285 B2 | 8/2013 | Lee et al. | |
| 8,546,576 B2 | 10/2013 | Lee et al. | |
| 2007/0264346 A1* | 11/2007 | Guimberteau | A61K 9/5073 424/488 |
| 2009/0221687 A1 | 9/2009 | Mesic et al. | |
| 2009/0227562 A1 | 9/2009 | Hughes | |
| 2009/0306140 A1 | 12/2009 | Lee et al. | |
| 2009/0318520 A1 | 12/2009 | Kovacs et al. | |

FOREIGN PATENT DOCUMENTS

| | | | |
|---|---|---|---|
| DK | WO 2009016214 A2 * | 2/2009 | .......... C07D 211/26 |
| WO | 2013039956 A2 | 3/2013 | |

OTHER PUBLICATIONS

Gu et al., "Stable Expression of Biogenic Amine Transporters Reveals Differences in Inhibitor Sensitivity, Kinetics, and Ion Dependence." J Biol Chem., 1994, 269, 10, p. 7124-7130.
Galli, et al., "Sodium-Dependent Norepinephrine-Induced Currents in Norepinphrine-Transporter-Transfected HEK-293 Cells Blocked by Cocaine and Antidepressants." J Exp Biol., 1995, 198, p. 2197-2212.
Pristupa, et al., "Pharmacological Heterogeneity of the Cloned and Native Human Dopamine Transporter: Disassociation of [3H]WIN 35,428 and [3H]GBR 12,935 Binding.", Mol Pharmacol., 1994, p. 125-135.
Han et al., "A novel serotonin-preferred triple reuptake inhibitor, SKL10406, has competitive and tolerable anti-depression profile." European Neuropsychopharmacology vol. 22 Oct. 2012. p. S272-S273, P.2.d.009.
Tran et al., "Efficacy and tolerability of the novel triple reuptake inhibitor amitifadine in the treatment of patients with major depressive disorder: A randomized, double-blind, placebo-controlled trial.", J of Psychiatric Research 46, 2012, p. 64-71.
Warnock et al., "Amitifadine, a triple monoamine uptake inhibitor reduces binge drinking and negative affect in an animal model of co-occurring alcoholism and depression symptomatology.", Pharmacol Biochem Behav. Nov. 2012; 103(1), p. 111-118.
University of Toronto Psychiatry, Annual Report 2010-2011, Toronto, Ontario, Canada.
SK holdings received approval from FDA to initiate clinical trials of the drug for depression, SK News, Fast and Accurate SK News, Nov. 2, 2009; accessed web address: http://www.sk.com/Channel/News/view/967, Jan. 27, 2014.
Pharmaceutical Research Companies Are Developing Nearly 200 Medicines to Treat Mental Illnesses and Addictive Disorders, Medicines in Development: Mental Illnesses, by America's Biopharmaceutical Research Companies, 2012 Report; Pharmaceutical Research and Manufacturers of America, Washington, DC.
Diagnostic and Statistical Manual of Mental Disorders, Fifth Edition (DSM-V), 2013, American Psychiatric Publishing, a division of American Psychiatric Association, Washington, DC.
Diagnostic and Statistical Manual of Mental Disorders, Fourth Edition (Text Revision) (DSM-IV-TR) 2000, American Psychiatric Association, Washington, DC.
Ahmed, et al. "Volumetric Structural Magnetic Resonance Imaging Findings in Pediatric Posttraumatic Stress Disorder and Obsessive Compulsive Disorder: A Systematic Review." Frontiers in Psychology 2012, v. 3, p. 1-11.
Mello, "A Review of Methods to Induce Alcohol Addiction in Animals." Pharmacol. Biochem. Be. 1973, v. 1, p. 89-101.
Volkow, "Cocaine." National Institute of Drug Abuse 2010, p. 1-7.
Written Opinion of the International Searching Authority for related application PCT/US14/17868, May 14, 2014.
International Search Report of the International Searching Authority for related application PCT/US14/17868, May 14, 2014.
Pennings, et al. "Effects of concurrent use of alcohol and cocaine" Addiction, 2002, 97(7), 773-783.
Pechnick et al. "The role of antagonism of NMDA receptor-mediated neurotransmission and inhibition of the dopamine reuptake in the neuroendocrine effects of phencyclidine" Life Sciences 2006, 78, 2006-2011.
Kranzler, et al. "Naltrexone vs. Nefazodone for Treatment of Alcohol Dependence" Neuropsychopharmacology 2000, 22, 493-503.
Moreno-Sanz, et al. "Administration of MDMA to ethanol-deprived rats increases ethanol operant self-administration and dopamine release during reinstatement." Int J Neuropsychopharmacol 2009, 12(7), 929-940.
Declaration by Thomas F. Newton, M.D., May 31, 2016.

* cited by examiner

Primary Examiner — Sarah Pihonak
(74) Attorney, Agent, or Firm — Norton Rose Fulbright US LLP

(57) ABSTRACT

Treatments are described for stress disorders and substance use disorders, for example, substance use disorders associated with use of alcohol, cocaine, amphetamines, and the like.

9 Claims, 12 Drawing Sheets

| TABLE 1 | | | |
|---|---|---|---|
| Inhibition % at 100 nM | | | |
| Example Compound | 5-HT reuptake | NE reuptake | DA reuptake |
| EC 1 | 81% | 94% | 88% |
| EC 2 | 98% | 85% | 85% |
| EC 10 | 93% | 87% | 93% |
| EC 12 | 83% | 90% | 92% |
| EC 13 | 84% | 87% | 63% |
| EC 14 | 76% | 70% | 52% |
| EC 15 | 75% | 98% | 99% |
| EC 35 | 76% | 72% | 78% |
| EC 67 | 97% | 90% | 81% |
| EC 68 | 96% | 57% | 63% |
| EC 70 | 95% | 14% | 3% |
| EC 71 | 92% | 46% | 54% |
| EC 72 | 86% | 6% | 2% |
| EC 75 | 86% | −1% | 41% |
| EC 80 | 59% | 55% | 84% |
| EC 83 | 96% | 78% | 66% |
| EC 84 | 44% | 5% | −4% |
| EC 85 | 94% | 74% | 81% |
| EC 86 | 93% | −1% | 35% |
| EC 90 | 87% | 39% | 44% |

(PRIOR ART)
FIG. 1

| TABLE 2 | |
|---|---|
| Example Compound | Reduction % at 30ip |
| EC 1 | 56.3% |
| EC 2 | 37.5% |
| EC 12 | 9.7% |
| EC 13 | 9.4% |
| EC 14 | 6.4% |
| EC 15 | 96.5% |
| EC 35 | 32.7% |
| EC 67 | 2.4% |
| EC 68 | 7.1% |
| EC 71 | 54.0% |
| EC 72 | 46.7% |
| EC 83 | 51.8% |
| EC 85 | 11.3% |
| EC 86 | 13.4% |

(PRIOR ART)
FIG. 2

| TABLE 3 | |
|---|---|
| Example Compound | Reduction % at 30ip |
| EC 1 | 57.5% (at 10ip) |
| EC 2 | 67.5% (at 20ip) |
| EC 12 | 91.8% |
| EC 15 | 75.3% |
| EC 71 | 86.0% |
| EC 83 | 83.7% |

(PRIOR ART)
FIG. 3

| TABLE 4 | |
|---|---|
| Test Compound | Reduction % at 30sc |
| EC 1 | 70.8% |
| EC 2 | 60.6% (at 10sc) |
| EC 12 | 50.5% |
| EC 13 | 71.8% |
| EC 15 | 55.3% |
| EC 68 | 48.1% (at 10sc) |
| EC 71 | 48.7% |
| EC 83 | 84.1% |
| EC 85 | 46.4% (at 10sc) |

(PRIOR ART)
FIG. 4

| Table 5 | Transporter binding, $IC_{50}$, nM | | |
|---|---|---|---|
| | SERT | NET | DAT |
| Example Compound 2 | 20 | 10 | 11 |
| Amitifadine | 12 | 23 | 96 |
| DOV 102,677 | 74 | 103 | 22 |

FIG. 5

Table 6

| Parameter | 25mg bid | | 75mg qd | | 50mg bid | | 75mg bid | | 100mg bid | |
|---|---|---|---|---|---|---|---|---|---|---|
| | Day 1 | Day 6 | Day 1 | Day 6 | Day 1 | Day 6 | Day 5 | Day 11 | Day 5 | Day 11 |
| $C_{max}$ (ng/mL) | 125 | 180 | 270 | 459 | 157 | 262 | 396 | 467 | 378 | 560 |
| $T_{max}$ (hr) - median | 1 | 1 | 1 | 1 | 1 | 1 | 1.5 | 1.5 | 1.5 | 1.25 |
| $AUC_{0-last}$ (ng*/hr/mL) | 769 | 1338 | 1597 | 2656 | 840 | 1728 | 2133 | 3575 | 1870 | 2793 |
| $AUC_{0-tau}$ (ng*/hr/mL) | 644 | 1077 | 1597 | 2656 | 760 | 1447 | 2139 | 3004 | 1871 | 2536 |
| $t_{½}$ (hr) | 5.62 | 7.4 | 4.81 | 5.33 | 4.69 | 6.75 | 3.5 | 6.49 | 2.55 | 6.21 |

FIG. 9

Table 7

| AE | Placebo N (%) | 25 mg bid N (%) | 75 mg qd N (%) | 50 mg bid N (%) | 75 mg bid N (%) | 100 mg bid N (%) | All Doses N (%) |
|---|---|---|---|---|---|---|---|
| Sample size (N) | 15 | 7 | 9 | 7 | 7 | 7 | 37 |
| Palpitation | 1 (6.7) | 0 | 0 | 0 | 0 | 1 (14.3) | 1 (2.7) |
| POTS | 1 (6.7) | 0 | 0 | 0 | 0 | 3 (42.9) | 3 (8.1) |
| Hearing Impaired | 0 | 0 | 0 | 0 | 0 | 1 (14.3) | 1 (2.7) |
| Hypothyroidism | 0 | 0 | 1 (11.1) | 0 | 0 | 1 (14.3) | 1 (2.7) |
| Visual Impairment | 0 | 0 | 0 | 0 | 0 | 1 (14.3) | 1 (2.7) |
| Abdominal Discomfort | 0 | 1 (14.3) | 0 | 0 | 0 | 0 | 1 (2.7) |
| Abdominal Pain | 1 (6.7) | 0 | 1 (11.1) | 1 (14.3) | 0 | 0 | 2 (5.4) |
| Diarrhea | 1 (6.7) | 0 | 0 | 0 | 0 | 0 | 0 |
| Nausea | 0 | 2 (28.6) | 6 (66.7) | 3 (42.9) | 4 (57.1) | 4 (57.1) | 19 (51.4) |
| Vomiting | 0 | 0 | 3 (33.3) | 1 (14.3) | 1 (14.3) | 0 | 5 (13.5) |
| Asthenia | 0 | 0 | 1 (11.1) | 0 | 0 | 0 | 1 (2.7) |
| Chest Discomfort | 1 (6.7) | 0 | 0 | 0 | 0 | 1 (14.3) | 1 (2.7) |
| Chills | 0 | 0 | 1 (11.1) | 0 | 0 | 0 | 1 (2.7) |
| Facial Pain | 1 (6.7) | 0 | 0 | 0 | 0 | 1 | 1 (2.7) |
| Fatigue | 0 | 0 | 1 (11.1) | 0 | 0 | 0 | 1 (2.7) |
| Blood Glucose Increased | 0 | 0 | 0 | 0 | 0 | 1 (14.3) | 1 (2.7) |
| Triglyceride Increased | 1 (6.7) | 0 | 0 | 0 | 0 | 0 | 0 |
| Decreased Appetite | 0 | 1 (14.3) | 0 | 0 | 0 | 0 | 1 (2.7) |
| Muscle Twitching | 0 | 0 | 1 (11.1) | 0 | 0 | 0 | 1 (2.7) |

FIG. 10

TREATMENT FOR SUBSTANCE USE DISORDERS AND STRESS DISORDERS

CROSS-REFERENCE TO RELATED APPLICATIONS

This application claims priority from U.S. Provisional Patent Application No. 61/767,886, filed on Feb. 22, 2013, the entirety of which is incorporated herein by reference.

BACKGROUND

Alcohol dependence is a major medical, social, and legal concern. The economic costs of alcohol dependence in the U.S. are estimated to be around $100 billion per year. Three medications are currently FDA-approved as treatments: disulfuram, acamprosate and naltrexone. Disulfuram has numerous limitations, including dangers from the disulfuram/alcohol reaction and poor treatment adherence. Acamprosate has not been shown to be more effective than placebo in studies conducted in the U.S.; approval was based on positive European studies. Slightly better efficacy outcomes have been obtained for naltrexone, although efficacy is limited to specific genotypes. While not specifically FDA-approved, topiramate is an effective treatment for alcohol dependence. However, in clinical practice, patients find its side effects difficult to tolerate, limiting its effectiveness. Reflecting the poor efficacy of existing treatments, acamprosate (Campral) sales remained barely above $80 million in 2010, whereas injectable naltrexone (Vivitrol) sales were below $25 million in 2012. Together, these figures may indicate that relatively few patients with alcohol dependence receive an effective medication treatment, underscoring an enormous untapped need, as between 5 and 10% of the U.S. population is estimated to have an alcohol use disorder.

The present disclosure appreciates that treatment for substance use disorders and stress disorders may be a challenging endeavor.

SUMMARY

In one embodiment, a method for treating a stress disorder or a substance use disorder in a subject in need of therapy includes administering to the subject an effective amount of a compound represented by Formula I:

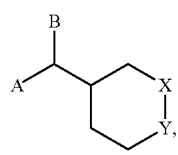
(I)

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl. In structural Formula I, B may be a moiety represented by a structural formula selected from Group II:

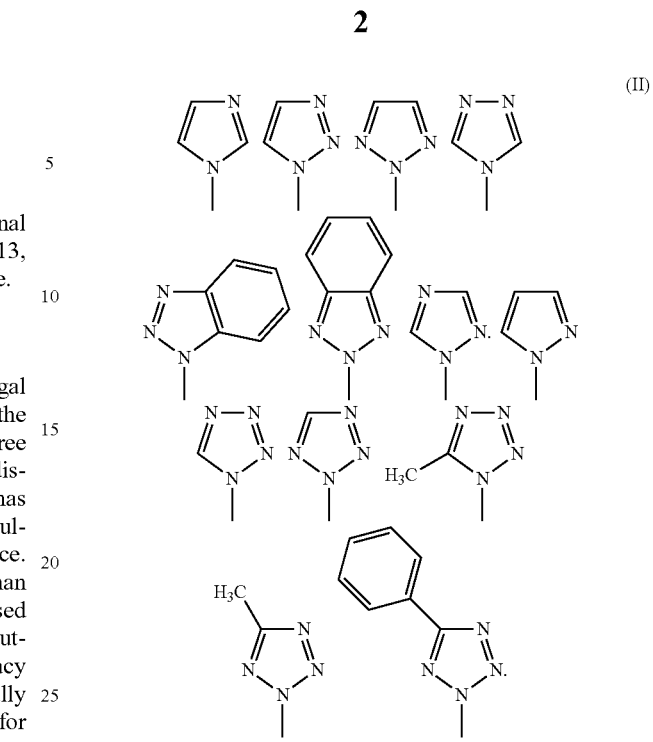

In structural Formula I, one of X and Y may be —$CH_2$— and the other may be —NR—. R may be H— or straight- or branched-chain $C_1$-$C_4$ alkyl.

In various embodiments, the stress disorder may include post-traumatic stress disorder (PTSD) and/or acute stress disorder (ASD).

In another embodiment, a kit for treating a stress disorder in a subject in need of therapy is provided. The kit may include an effective amount of a compound represented by Formula I:

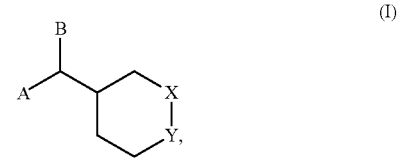
(I)

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl. In structural Formula I, B may be a moiety represented by a structural formula selected from Group II:

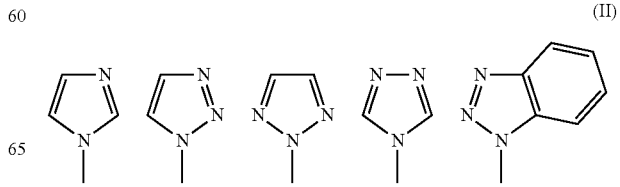
(II)

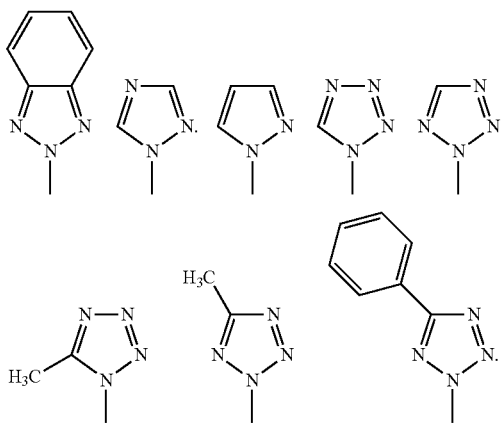

In structural Formula I, one of X and Y may be —CH$_2$— and the other may be —NR—. R may be H— or straight- or branched-chain C$_1$-C$_4$ alkyl. The kit may also include instructions for administering an effective amount of the compound to the subject to treat the stress disorder in the subject. In various embodiments, the stress disorder may include post-traumatic stress disorder (PTSD) and/or acute stress disorder (ASD).

In one embodiment, a kit for treating a substance use disorder in a subject in need of therapy is provided. The kit may include a compound represented by Formula I:

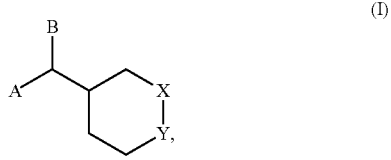

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain C$_1$-C$_4$ alkyl, straight- or branched-chain C$_1$-C$_3$ alkoxy, nitro, cyano, trifluoromethyl, trifluoromethoxy, methanesulfonyl, phenyloxy, phenyl, and thienyl. In structural Formula I, B may be a moiety represented by a structural formula selected from Group II:

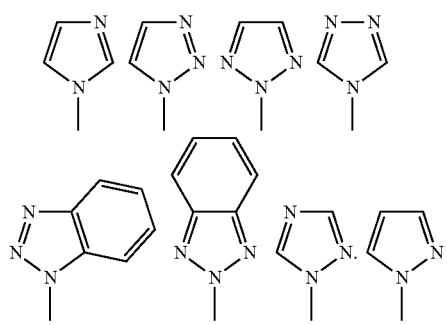

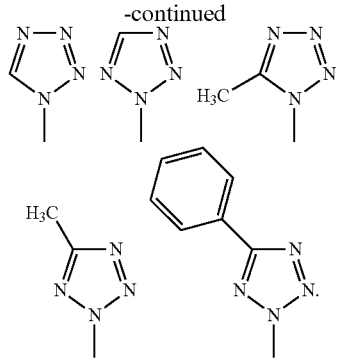

In structural Formula I, one of X and Y may be —CH$_2$— and the other may be —NR—. R may be H— or straight- or branched-chain C$_1$-C$_4$ alkyl.

The kit may also include instructions for administering an effective amount of the compound to the subject to treat the substance use disorder in the subject. The substance use disorder may be one or more of an alcohol use disorder or a stimulant use disorder.

BRIEF DESCRIPTION OF THE DRAWINGS

The accompanying figures, which are incorporated in and constitute a part of the specification, illustrate example methods and apparatuses, and are used merely to illustrate example embodiments.

FIG. 1 shows Table 1 (PRIOR ART), which includes sample values reported for various Example Compounds described herein according to Examples 1, 2, and 3.

FIG. 2 shows Table 2 (PRIOR ART), which includes sample values reported for various Example Compounds described herein for the forced swimming test in mice according to Example 4.

FIG. 3 shows Table 3 (PRIOR ART), which includes sample values reported for various Example Compounds described herein for the marble burying test in mice according to Example 5.

FIG. 4 shows Table 4 (PRIOR ART), which includes sample values reported for various Example Compounds described herein for the acetic acid induced writhing test in mice according to Example 6.

FIG. 5 shows Table 5, which includes the IC$_{50}$ binding profiles for Example Compound 2, amitifadine, and DOV 102,677 at the three corresponding monoamine transporter proteins according to Example 7.

FIG. 9 shows Table 6, which includes safety and pharmacokinetics results of a multiple ascending dose study in healthy volunteers for Example Compound 2 according to Example 14.

FIG. 10 shows Table 7, which includes adverse event data for a multiple ascending dose study in healthy volunteers for Example Compound 2 according to Example 14.

DETAILED DESCRIPTION

Figure 6A:
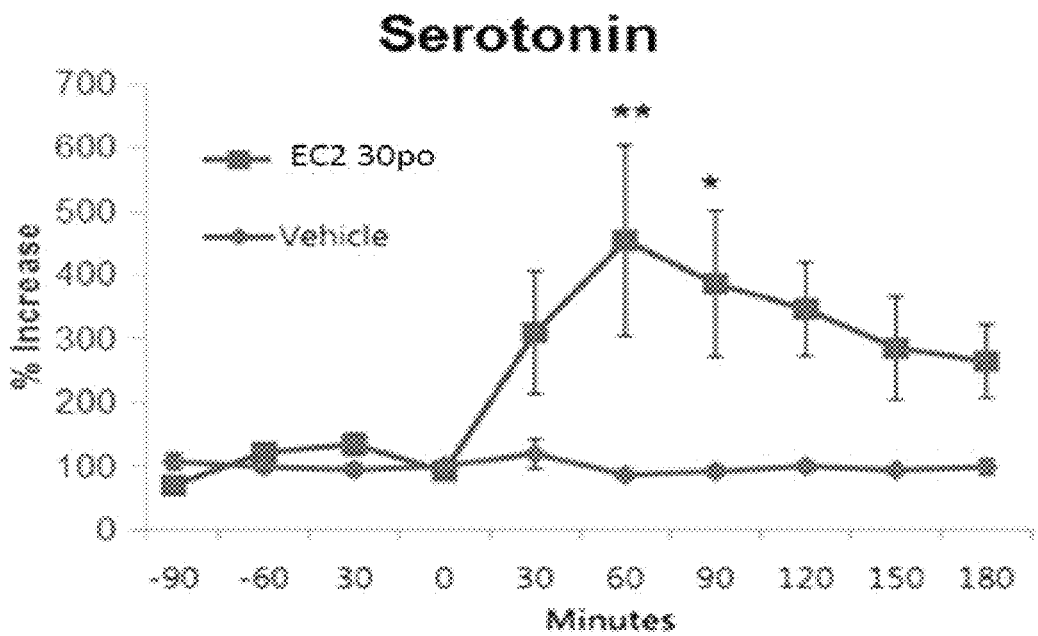
FIGS. 6A, 6B, and 6C are graphs showing the effect of oral treatment with Example Compound 2 on synaptic levels of serotonin, norepinephrine, and dopamine, respectively, in rat prefrontal cortex according to Example 8.

In one embodiment, a method for treating a stress disorder or a substance use disorder in a subject in need of therapy includes administering to the subject an effective amount of a compound represented by Formula I:

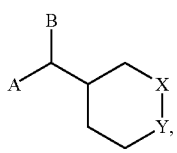
(I)

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl.

In structural Formula I, B may be a moiety represented by a structural formula selected from Group II:

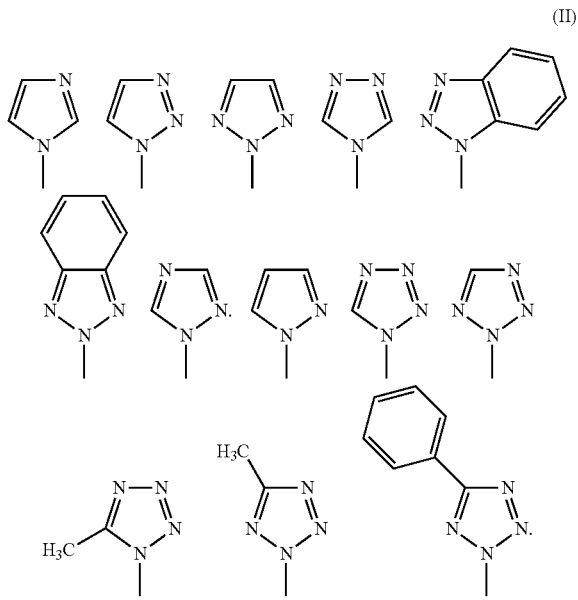
(II)

In structural Formula I, one of X and Y may be —CH$_2$— and the other may be —NR—. R may be H— or straight- or branched-chain $C_1$-$C_4$ alkyl.

In various embodiments, the substance use disorder may include any substance use disorder as defined in the *Diagnostic and Statistical Manual of Mental Disorders* V (DSM-V) (5th ed., American Psychiatric Association, Washington, D.C., 2013), the entire contents of which are incorporated herein by reference. Substance use disorders may be briefly outlined as follows. For example, the substance use disorder may include an alcohol use disorder. The substance use disorder may include a stimulant use disorder, e.g., a disorder arising from the use of cocaine or an amphetamine. An amphetamine may include amphetamine, substituted amphetamine derivatives such as methamphetamine, enantiomers or stereoisomers thereof, metabolites or prodrugs thereof, salts thereof, and the like. The substance use disorder may be associated with any behavior or symptom which may be associated with the substance use disorder, such as abuse, tolerance, drug-seeking behavior, physiological side effects, and the like. For example, abuse may include binge consumption, e.g., binge drinking of ethanol.

In some embodiments, the method is directed to treating stress disorders such as post-traumatic stress disorder (PTSD) and/or acute stress disorder (ASD) (PTSD/ASD) in a subject in need of therapy by administering to the subject an effective amount of the compound represented by Formula I. As used herein, PTSD and ASD refers to the diagnostic criteria for post-traumatic stress disorder and acute stress disorder provided in the *Diagnostic and Statistical Manual of Mental Disorders* V (DSM-V) (5th ed., American Psychiatric Association, Washington, D.C., 2013), the entire contents of which are incorporated herein by reference. The diagnostic criteria for PTSD and ASD may be summarized briefly as follows:

Criterion A, Stressor: The person was exposed to: death, threatened death, actual or threatened serious injury, or actual or threatened sexual violence, as follows (one required): direct exposure; witnessing, in person; indirectly, by learning that a close relative or close friend was exposed to trauma (if the event involved actual or threatened death, it must have been violent or accidental); or repeated or extreme indirect exposure to aversive details of the event(s), usually in the course of professional duties (e.g., first responders, collecting body parts; professionals repeatedly exposed to details of child abuse. This does not include indirect non-professional exposure through electronic media, television, movies, or pictures.)

Criterion B, Intrusion Symptoms: The traumatic event is persistently re-experienced in the following way(s) (one required): recurrent, involuntary, and intrusive memories. (note: children older than six may express this symptom in repetitive play); traumatic nightmares (note: children may have frightening dreams without content related to the trauma(s)); dissociative reactions (e.g., flashbacks) which may occur on a continuum from brief episodes to complete loss of consciousness (note: children may reenact the event in play); intense or prolonged distress after exposure to traumatic reminders; or marked physiologic reactivity after exposure to trauma-related stimuli.

Criterion C, Avoidance: Persistent effortful avoidance of distressing trauma-related stimuli after the event (one required): trauma-related thoughts or feelings; or trauma-related external reminders (e.g., people, places, conversations, activities, objects, or situations).

Criterion D: Negative Alterations in Cognitions and Mood: Negative alterations in cognitions and mood that began or worsened after the traumatic event (two required): inability to recall key features of the traumatic event (usually dissociative amnesia; not due to head injury, alcohol, or drugs); persistent (and often distorted) negative beliefs and expectations about oneself or the world (e.g., "I am bad," "the world is completely dangerous"); persistent distorted blame of self or others for causing the traumatic event or for resulting consequences; persistent negative trauma-related emotions (e.g., fear, horror, anger, guilt, or shame); markedly diminished interest in (pre-traumatic) significant activities; feeling alienated from others (e.g., detachment or estrangement); or constricted affect: persistent inability to experience positive emotions.

Criterion E, Alterations in Arousal and Reactivity: Trauma-related alterations in arousal and reactivity that began or worsened after the traumatic event (two required): Irritable or aggressive behavior; Self-destructive or reckless behavior, Hypervigilance; Exaggerated startle response; Problems in concentration; or Sleep disturbance Criterion F, Duration: Persistence of Symptoms (in Criteria B, C, D, and E) for more than one month; symptoms persisting less than one month may be termed acute stress disorder (ASD).

Criterion G, Functional significance: Significant symptom-related distress or functional impairment (e.g., social, occupational).

Figure 7A:
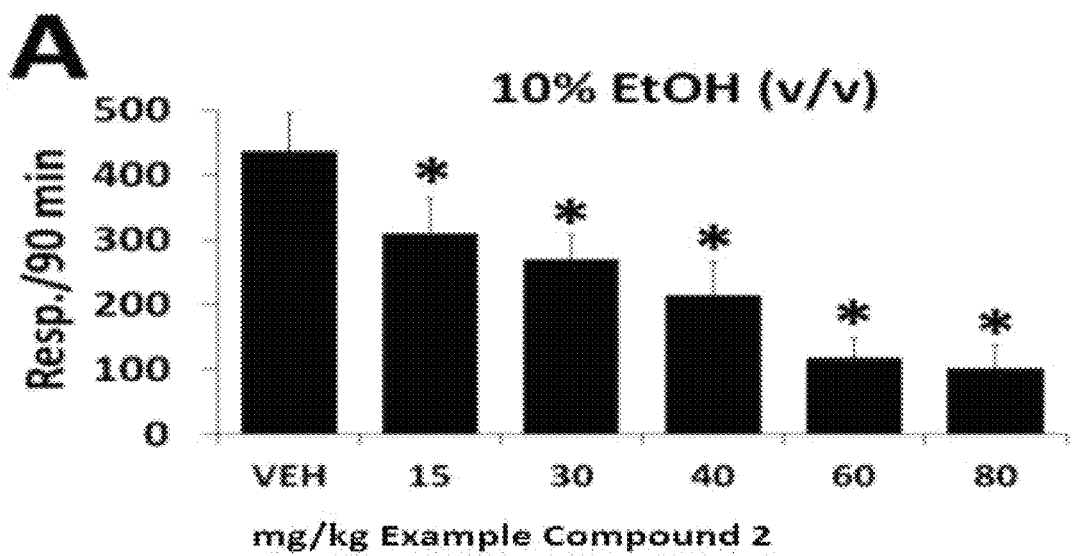
FIGS. 7A and 7B are graphs showing the effect of oral treatment with Example Compound 2 on binge alcohol drinking and sucrose drinking, respectively, in alcohol preferring rats according to Example 8.
Figure 8:
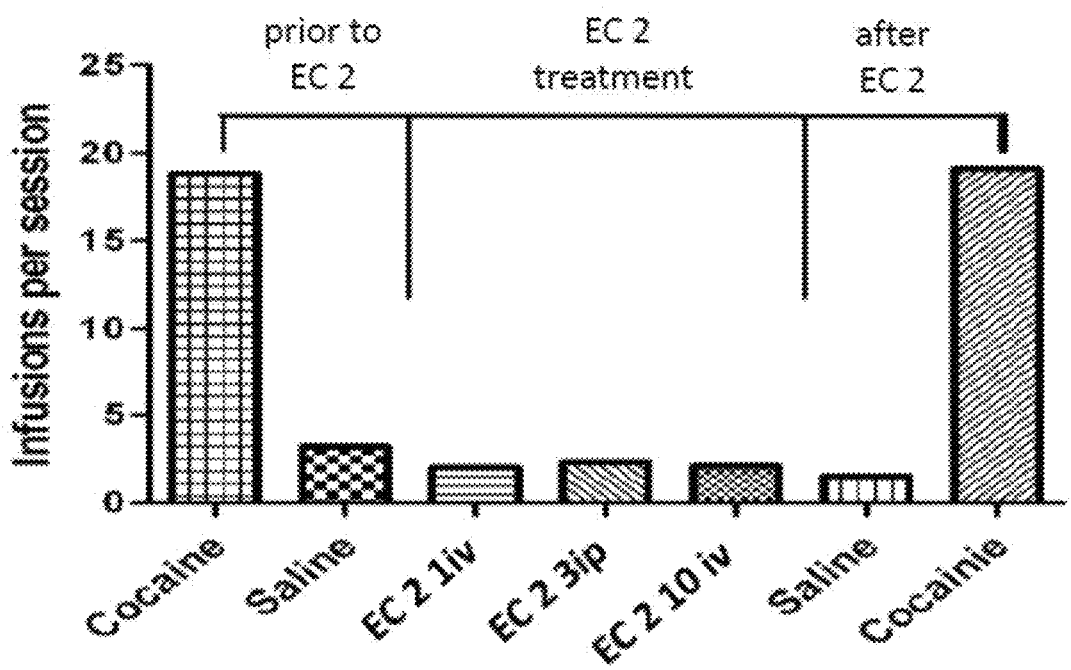
FIG. 8 is a graph showing that Example Compound 2 is not self-administered in rats according to Example 11, which is indicative of low abuse potential.

Various animal models for PTSD and/or ASD are known but remain controversial. Nevertheless, it is believed that combined observations and new data of the Examples strongly suggest use of the compounds represented by Formula I for treatment of PTSD and/or ASD. For instance, Example 7 and FIG. 5 shows relatively balanced $IC_{50}$ binding profiles for Example Compound 2 at the three corresponding recombinant human monoamine transporter proteins compared to structurally unrelated compounds which may be relevant to treating a complex condition like PTSD/ASD. Also, Example 8, FIG. 7A shows the effect of oral treatment with Example Compound 2 on binge alcohol drinking, which may share some symptoms with PTSD/ASD. Further, Example 11, FIG. 8 shows that Example Compound 2 may have low abuse potential, a desirable factor in treating individuals with PTSD/ASD, who may be susceptible to self-medicating behaviors. Moreover, Example 14, FIGS. 9 and 10, includes safety, pharmacokinetics, and adverse effects in healthy volunteers for Example Compound 2, which is important for considering administration to human subjects, currently the only subjects known to be capable of exhibiting PTSD/ASD. Also, Example 16 and 17, FIGS. 11A-12B show the effects on locomotor activation for combined administration of methamphetamine and Example Compound 2, which effects may suggest activity against PTSD/ASD symptoms such as marked physiologic reactivity, persistent effortful avoidance of distressing trauma-related stimuli; negative alterations in cognitions and mood; trauma-related alterations in arousal and reactivity, and the like. These observations are further supported by prior art data shown in Example 4, FIG. 2 which relates various Example Compounds to treatment of model depression symptoms; Example 5, FIG. 3, which relates various Example Compounds to treatment of anxiety symptoms; and Example 6, FIG. 4 which relates various Example Compounds to treatment of pain symptoms. The symptoms of these prior art experiments do not together constitute PTSD/ASD. However, the results may, in combination with the new results in the remaining Examples, tend to support addressing some individual criteria for PTSD/ASD.

In some embodiments, the reuptake inhibition percentages at 100 nM for each of the serotonin, norepinephrine, and dopamine transporters may have a subtractive difference in percent of less than about a selected percent value. For instance, Example Compound 14 has reuptake inhibition percentages at 100 nM for each of the serotonin, norepinephrine, and dopamine transporters of 76%, 70%, and 52%, respectively. See FIG. 1, Table 1, and Examples 1, 2, and 3. Therefore, the reuptake inhibition percentages for Example Compound 14 may have a subtractive difference of, at most, 76%–52%=24%. In various embodiments, the reuptake inhibition percentages at 100 nM for each of the serotonin, norepinephrine, and dopamine transporter proteins for a compound of the method may have a subtractive difference in percent, at most, of less than about 30, 25, 20, 19, 18, 17, 16, 15, 14, 13, 12, 11, 10, 9, 8, 7, 6, 5, 4, 3, 2, or 1. For example, the compound represented by structural Formula I may be characterized by reuptake inhibition percentages at 100 nM for each of human serotonin, human norepinephrine, and human dopamine transporter proteins such that the reuptake inhibition percentages at 100 nM have a subtractive difference at most of less than about 30%.

In some embodiments, the $IC_{50}$ binding concentrations at each of the serotonin, norepinephrine, and dopamine transporter proteins may differ at most by a ratio of less than a selected value. For example, the $IC_{50}$ binding concentrations at each of the serotonin, norepinephrine, and dopamine transporter proteins for Example Compound 2 are 20 nM, 10 nM, and 11 nM, respectively. See Example 7. Therefore, the $IC_{50}$ binding concentrations for Example Compound 2 differ by at most a ratio of 20:10 or 2:1. In various embodiments, the $IC_{50}$ binding concentrations for the serotonin, norepinephrine, and dopamine transporter proteins for a compound of the method may differ at most by a ratio of less than 4:1 or less than about 3.75:1, 3.5:1, 3.25:1, 3:1, 2.75:1, 2.5:1, 2.25:1, 2:1, 1.75:1, 1.5:1, or 1.25:1. For example, the compound represented by structural Formula I may be characterized by relative $IC_{50}$ binding concentrations for human serotonin, human norepinephrine, and human dopamine transporter proteins such that the relative $IC_{50}$ binding concentrations differ at most by a ratio of less than 4:1.

In some embodiments, the sum of the $IC_{50}$ binding concentrations for the serotonin, norepinephrine, and dopamine transporter proteins may be less than a selected nM value. For example, the $IC_{50}$ binding concentrations at each of the serotonin, norepinephrine, and dopamine transporter proteins for Example Compound 2 are 20 nM, 10 nM, and 11 nM, respectively. See Example 7. Therefore, the sum of the $IC_{50}$ binding concentrations for Example Compound 2 may be 41 nM. In various embodiments, the sum of the $IC_{50}$ binding concentrations for each of the serotonin, norepinephrine, and dopamine transporter proteins for a compound of the method may be a value in nM of less than 131 or less than about 130, 125, 120, 115, 110, 105, 100, 95, 90, 85, 80, 75, 70, 65, 60, 55, 50, 45, 41, 40, 35, 30, 25, 20, 15, 10, or 5. For example, the compound represented by structural Formula I may be characterized by $IC_{50}$ binding concentrations for human serotonin, human norepinephrine, and human dopamine transporter proteins such that a sum of the $IC_{50}$ binding concentrations may be less than 131 nM.

In several embodiments, the compound may be represented by a structural formula selected from Group III:

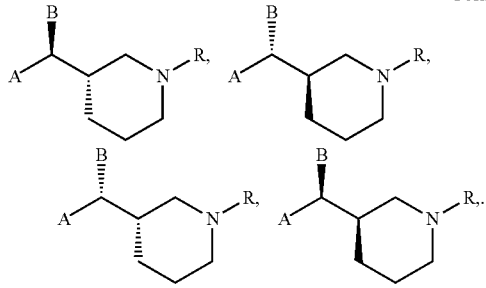

Formulae (III)

or a pharmaceutically acceptable salt thereof.

In some embodiments, the compound may be represented by a structural formula selected from Group IV:

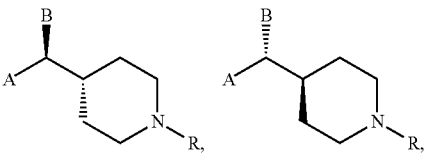

Formulae (IV)

or a pharmaceutically acceptable salt thereof.

In various embodiments, the compound may be represented by a structural formula selected from Group XXII, or a pharmaceutically acceptable salt thereof:

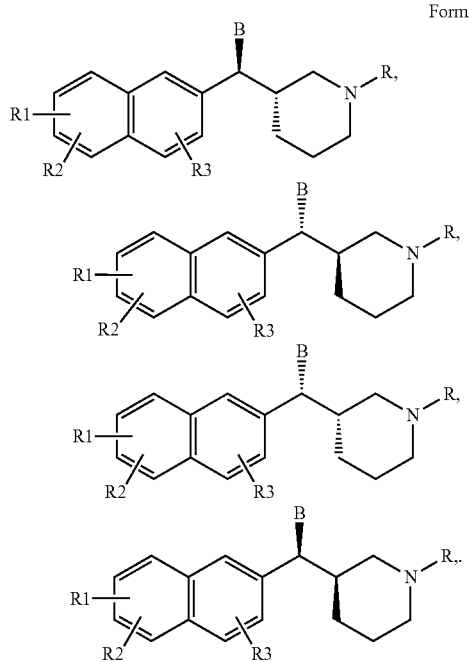

Formulae (XXII)

Each of $R_1$, $R_2$, and $R_3$ may be independently selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl.

In several embodiments, B in the compound may be:

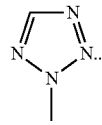

In some embodiments, each of $R_1$, $R_2$, and $R_3$ may be independently selected from H—, halo, methyl, and methoxy.

In various embodiments, the compound may be enantiomerically enriched. For example, the compound may be in a mix of enantiomers, e.g., a mixture of Example Compounds 1 and 2, of which one enantiomeric compound, e.g., Example Compound 2, may be in a molar percentage compared to the total moles of all enantiomeric compounds of the method in the mixture by at least about 51%, 55%, 60%, 65%, 70%, 75%, 80%, 85%, 90%, 95%, 96%, 97%, 98%, 99%, 99.5%, 99.6%, 99.7%, 99.8%, or 99.9%. Mixtures of enantiomers, for example racemic mixtures, may be separated into enantiomers or may be enantiomerically enriched by techniques and procedures readily available to one of ordinary skill in the art. Further details of separating or enriching enantiomers of the compounds represented by structural Formula I and pharmaceutical acceptable salts thereof, e.g., the Example Compounds, may be found in U.S. Pat. Nos. 8,513,285 and 8,546,576, the entire contents of which are incorporated by reference herein.

In various embodiments, A may be naphthyl optionally substituted with one or more identical or different substituents selected from hydrogen, halogen, straight- or branched-chain alkyl of from 1 to 4 carbon atoms, straight- or branched-chain alkoxy of from 1 to 3 carbon atoms, nitro, cyano, trifluoromethyl, trifluoromethoxy, methanesulfonyl, phenyloxy, phenyl, and thienyl.

In some embodiments, B may be an azole selected from triazole, benzotriazole, tetrazole, 5-methyl tetrazole, and 5-phenyl tetrazole, which are linked by nitrogen represented by a structural formula selected from:

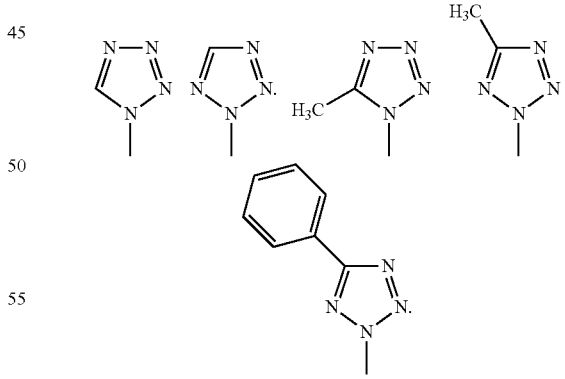

In several embodiments, the compound may be any one of Example Compounds 1-126:

1 (3R)-3-[(R)-naphthalen-2-yl(2H-tetrazol-2-yl)methyl]piperidine
2 (3S)-3-[(S)-naphthalen-2-yl(2H-tetrazol-2-yl)methyl]piperidine
3 (3R)-3-[(S)-naphthalen-2-yl(2H-tetrazol-2-yl)methyl]piperidine 4 (3S)-3-[(R)-naphthalen-2-yl(2H-tetrazol-2-yl)methyl]piperidine
5 (3R)-3-[(R)-naphthalen-2-yl(1H-tetrazol-1-yl)methyl]piperidine
6 (3S)-3-[(S)-naphthalen-2-yl(1H-tetrazol-1-yl)methyl]piperidine
7 (3R)-3-[(S)-naphthalen-2-yl(1H-tetrazol-1-yl)methyl]piperidine
8 (3S)-3-[(R)-naphthalen-2-yl(1H-tetrazol-1-yl)methyl]piperidine
9 (3S)-3-[(R)-(5-methyl-2H-tetrazol-2-yl)(naphthalen-2-yl)methyl]piperidine
10 (3S)-3-[(S)-(5-methyl-2H-tetrazol-2-yl)(naphthalen-2-yl)methyl]piperidine
11 (3R)-3-[(S)-(5-methyl-2H-tetrazol-2-yl)(naphthalen-2-yl)methyl]piperidine
12 (3R)-3-[(R)-(5-methyl-2H-tetrazol-2-yl)(naphthalen-2-yl)methyl]piperidine
13 (3R)-3-[(R)-naphthalen-2-yl(2H-1,2,3-triazol-2-yl)methyl]piperidine
14 (3S)-3-[(S)-naphthalen-2-yl(2H-1,2,3-triazol-2-yl)methyl]piperidine
15 (3R)-3-[(R)-(3,4-dichlorophenyl(2-tetrazol-2-yl)methyl]piperidine
16 (3S)-3-[(S)-(3,4-dichlorophenyl)(2H-tetrazol-2-yl)methyl]piperidine
17 (3R)-3-[(R)-(4-chlorophenyl)(2H-tetrazol-2-yl)methyl]piperidine
18 (3S)-3-[(S)-(4-chlorophenyl)(2H-tetrazol-2-yl)methyl]piperidine
19 (3R)-3-[(S)-(4-chlorophenyl)(2H-tetrazol-2-yl)methyl]piperidine
20 (3S)-3-[(R)-(4-chlorophenyl)(2H-tetrazol-2-yl)methyl]piperidine
21 (3R)-3-[(R)-naphthalen-1-yl)(2H-tetrazol-2-yl)methyl]piperidine
22 (3S)-3-[(S)-naphthalen-1-yl)(2H-tetrazol-2-yl)methyl]piperidine
23 (3R)-3-[(R)-(4-isopropylphenyl)(2H-tetrazol-2-yl)methyl]piperidine
24 (3S)-3-[(S)-(4-isopropylphenyl)(2H-tetrazol-2-yl)methyl]piperidine
(3R)-3-[(S)-(4-isopropylphenyl)(2H-tetrazol-2-yl)methyl]piperidine
26 (3S)-3-[(R)-(4-isopropylphenyl)(2H-tetrazol-2-yl)methyl]piperidine
27 (3S)-3-[(S)-(3,4-dimethoxyphenyl)(2H-tetrazol-2-yl)methyl]piperidine
28 (3S)-3-[(R)-(3,4-dimethoxyphenyl)(2H-tetrazol-2-yl)methyl]piperidine
29 (3S)-3-[(S)-(3,4-dimethoxyphenyl)(1H-tetrazol-1-yl)methyl]piperidine
30 (3S)-3-[(R)-(3,4-dimethoxyphenyl)(1H-tetrazol-1-yl)methyl]piperidine
31 (3S)-3-[(S)-phenyl(2H-tetrazol-2-yl)methyl]piperidine
32 (3S)-3-[(R)-phenyl(2H-tetrazol-2-yl)methyl]piperidine
33 (3S)-3-{(S)-2H-tetrazol-2-yl[4-(trifluoromethyl)phenyl]methyl}piperidine
34 (3S)-3-{(R)-2H-tetrazol-2-yl[4-(trifluoromethyl)phenyl]methyl}piperidine
35 (3S)-3-[(S)-(6-methoxynaphthalen-2-yl)(2H-tetrazol-2-yl)methyl]piperidine
36 (3S)-3-[(R)-(6-methoxynaphthalen-2-yl)(2H-tetrazol-2-yl)methyl]piperidine
37 (3S)-3-[(S)-(4-methylphenyl)(2H-tetrazol-2-yl)methyl]piperidine
38 (3S)-3-[(R)-(4-methylphenyl)(2H-tetrazol-2-yl)methyl]piperidine
39 (3S)-3-[(S)-(3-chlorophenyl)(2H-tetrazol-2-yl)methyl]piperidine
40 (3S)-3-[(R)-(3-chlorophenyl)(2H-tetrazol-2-yl)methyl]piperidine
41 (3S)-3-[(S)-(2,4-difluorophenyl)(2H-tetrazol-2-yl)methyl]piperidine
42 (3S)-3-[(R)-(2,4-difluorophenyl)(2H-tetrazol-2-yl)methyl]piperidine
43 (3S)-3-[(S)-(4-methoxyphenyl)(2H-tetrazol-2-yl)methyl]piperidine
44 (3S)-3-[(R)-(4-methoxyphenyl)(2H-tetrazol-2-yl)methyl]piperidine
45 (3S)-3-[(S)-(4-methoxyphenyl)(1H-tetrazol-1-yl)methyl]piperidine
46 (3S)$_3$-[(R)-(4-methoxyphenyl)(1H-tetrazol-1-yl)methyl]piperidine
47 (3S)-3-[(S)-(4-phenoxyphenyl)(2H-tetrazol-2-yl)methyl]piperidine
48 (3S)-3-[(R)-(4-phenoxyphenyl)(2H-tetrazol-2-yl)methyl]piperidine
49 (3S)-3-[(S)-(4-phenoxyphenyl)(1H-tetrazol-1-yl)methyl]piperidine
50 (3S)-3-[(R)-(4-phenoxyphenyl)(1H-tetrazol-1-yl)methyl]piperidine
51 (3S)-3-[(S)-(4-fluorophenyl)(2H-tetrazol-2-yl)methyl]piperidine
52 (3S)-3-[(R)-(4-fluorophenyl)(2H-tetrazol-2-yl)methyl]piperidine
53 (3S)-3-[(S)-biphenyl-4-yl(2H-tetrazol-2-yl)methyl]piperidine
54 (3S)-3-[(R)-biphenyl-4-yl(2H-tetrazol-2-yl)methyl]piperidine
55 (3S)-3-{(S)-2H-tetrazol-2-yl[3-(trifluoromethyl)phenyl]methyl)}piperidine
56 (3S)-3-{(R)-2H-tetrazol-2-yl[3-(trifluoromethyl)phenyl]methyl}piperidine
57 (3S)-3-[(S)-(4-propylphenyl)(2H-tetrazol-2-yl)methyl]piperidine
58 (3S)-3-[(R)-(4-propylphenyl)(2H-tetrazol-2-yl)methyl]piperidine
59 (3S)-3-[(S)-(4-methoxynaphthalen-1-yl)(2H-tetrazol-2-yl)methyl]piperidine
60 (3S)-3-[(R)-(4-methylnaphthalen-1-yl)(2H-tetrazol-2-yl)methyl]piperidine
61 (3S)-3-[(S)-(3-methylphenyl)(2H-tetrazol-2-yl)-methyl]piperidine
62 (3S)-3-[(R)-(3-methylphenyl)(2H-tetrazol-2-yl)-methyl]piperidine
63 (3S)-3-[(R)-(3-methoxyphenyl)(2H-tetrazol-2-yl)methyl]piperidine
64 (3S)-3-[(R)-(3-methoxyphenyl)(2H-tetrazol-2-yl)methyl]piperidine
65 (3S)-3-[(S)-1-benzothiophen-5-yl(2H-tetrazol-2-yl)methyl]piperidine
66 (3S)-3-[(R)-1-benzothiophen-5-yl(2H-tetrazol-2-yl)methyl]piperidine
67 (3R)-3-[(R)-(6-chloronaphthalen-2-yl)(2H-tetrazol-2-yl)methyl]piperidine
68 (3S)-3-[(S)-(6-chloronaphthalen-2-yl)(2H-tetrazol-2-yl)methyl]piperidine
69 (3R)-3-[(S)-(6-chloronaphthalen-2-yl)(2H-tetrazol-2-yl)methyl]piperidine
70 (3S)-3-[(R)-(6-chloronaphthalen-2-yl)(2H-tetrazol-2-yl)methyl]piperidine 71 (3S)-3-[(S)-(6-fluoronaphthalen-2-yl)(2H-tetrazol-2-yl)methyl]piperidine
72 (3S)-3-[(R)-(6-fluoronaphthalen-2-yl)(2H-tetrazol-2-yl)methyl]piperidine
73 (3S)-1-ethyl-3-[(S)-naphthalen-2-yl(2H-tetrazol-2-yl)methyl]piperidine
74 (3R)-3-[(R)-naphthalen-2-yl(5-phenyl-tetrazol-2-yl)methyl]piperidine
75 (3S)-3-[(S)-naphthalen-2-yl(5-phenyl-tetrazol-2-yl)methyl]piperidine
76 (3R)-3-[(S)-naphthalen-2-yl(5-phenyl-tetrazol-2-yl)methyl]piperidine
77 (3S)-3-[(B)-naphthalen-2-yl(5-phenyl-tetrazol-2-yl)methyl]piperidine
78 1-{(S)-naphthalen-2-yl[(3S)-piperidin-3-yl]methyl)}-1H-benzotriazole
79 1-{(R)-naphthalen-2-yl[(3S)-piperidin-3-yl]methyl}-1H-benzotriazole
80 2-{(S)-naphthalen-2-yl[(3S)-piperidin-3-yl]methyl}-2H-benzotriazole
81 2-{(R)-naphthalen-2-yl[(3S)-piperidin-3-yl]methyl}-2H-benzotriazole
82 (3S)-3-[(R)-1-benzothiophen-3-yl(2H-tetrazol-2-yl)methyl]piperidine
83 (3R)-3-[(R)-(6-fluoronaphthalen-2-yl)(2H-tetrazol-2-yl)methyl]piperidine
84 (3R)-3-[(S)-(6-fluoronaphthalen-2-yl)(2H-tetrazol-2-yl)methyl]piperidine
85 (3S)-3-[(S)-(6-methylnaphthalen-2-yl)(2H-tetrazol-2-yl)methyl]piperidine
86 (3S)-3-[(R)-(6-methylnaphthalen-2-yl)(2H-tetrazol-2-yl)methyl]piperidine
87 (3S)-3-[(S)-(4-fluoronaphthalen-1-yl)(2H-tetrazol-2-yl)methyl]piperidine
88 (3S)-3-[(R)-(4-fluoronaphthalen-1-yl)(2H-tetrazol-2t-yl)methyl]piperidine
89 (3S)-3-[(R)-naphthalen-2-yl(4H-1,2,4-triazol-4-yl)methyl]piperidine
90 (3S)-3-[(S)-naphthalen-2-yl(1H-1,2,4-triazol-1-yl)methyl]piperidine
91 (3S)-3-[(R)-naphthalen-2-yl(1H-1,2,4-triazol-1-yl)methyl]piperidine
92 (3S)-3-[(R)-naphthalen-2-yl(1H-pyrazol-1-yl)methyl]piperidine
93 (3S)-3-[(S)-1-benzothiophen-2-yl(2H-tetrazol-2-yl)methyl]piperidine
94 (3S)-3-[(R)-1-benzothiophen-2-yl(2H-tetrazol-2-yl)methyl]piperidine
95 (3S)-3-[(S)-(3,4-difluorophenyl)(2H-tetrazol-2-yl)methyl]piperidine
96 (3S)-3-[(R)-(3,4-difluorophenyl)(2H-tetrazol-2-yl)methyl]piperidine
97 (3S)-3-[(S)-(2,3-dichlorophenyl)(2H-tetrazol-2-yl)methyl]piperidine
98 (3S)-3-[(R)-(2,3-dichlorophenyl)(2H-tetrazol-2-yl)methyl]piperidine
99 (3R)-3-[(R)-(1-fluoronaphthalen-2-yl)(2H-tetrazol-2-yl)methyl]piperidine
100 (3S)-3-[(S)-(1-fluoronaphthalen-2-yl)(1-H-tetrazol-2-yl)methyl]piperidine
101 (3R)-3-[(S)-(1-fluoronaphthalen-2-yl)(2H-tetrazol-2-yl)methyl]piperidine
102 (3S)-3-[(R)-(1-fluoronaphthalen-2-yl)(2H-tetrazol-2-yl)methyl]piperidine
103 (3R)-3-[(R)-(1-fluoronaphthalen-2-yl)(5-methyl-2H-tetrazol-2-yl)methyl]piperidine
104 (3S)-3-[(S)-(1-fluoronaphthalen-2-yl)(5-methyl-2H-tetrazol-2-yl)methyl]piperidine
105 (3R)-3-[(S)-(1-fluoronaphthalen-2-yl)(5-methyl-2H-tetrazol-2-yl)methyl]piperidine
106 (3S)-3-[(R)-(1-fluoronaphthalen-2-yl)(5-methyl-2H-tetrazol-2-yl)methyl]piperidine
107 (3R)-3-[(R)-(1-fluoronaphthalen-2-yl)(5-phenyl-2H-tetrazol-2-yl)methyl]piperidine
108 (3S)-3-[(S)-(1-fluoronaphthalen-2-yl)(5-phenyl-2H-tetrazol-2-yl)methyl]piperidine
109 (3R)-3-[(S)-(1-fluoronaphthalen-2-yl)(5-phenyl-2H-tetrazol-2-yl)methyl]piperidine
110 (3S)-3-[(R)-(1-fluoronaphthalen-2-yl)(5-phenyl-2H-tetrazol-2-yl)methyl]piperidine
111 (3R)-3-[(R)-(6-fluoronaphthalen-2-yl)(5-methyl-2H-tetrazol-2-yl)methyl]piperidine
112 (3S)-1-butyl-3-[naphthalen-2-yl(2H-tetrazol-2-yl)methyl]piperidine
113 4-[(S)-naphthalen-2-yl(2H-tetrazol-2-yl)methyl]piperidine
114 4-[(R)-naphthalen-2-yl(2H-tetrazol-2-yl)methyl]piperidine
115 4-[(S)-naphthalen-2-yl(1H-tetrazol-2-yl)methyl]piperidine
116 4-[(R)-naphthalen-2-yl(1H-tetrazol-2-yl)methyl]piperidine
117 4-[(S)-(4-methylphenyl)(2H-tetrazol-2-yl)methyl]piperidine
118 4-[(R)-(4-methylphenyl)(2H-tetrazol-2-yl)methyl]piperidine
119 4-[(S)-(4-methylphenyl)(1H-tetrazol-2-yl)methyl]piperidine
120 4-[(R)-(4-methylphenyl)(1H-tetrazol-2-yl)methyl]piperidine
121 4-[(S)-naphthalen-2-yl(2H-1,2,3-triazol-2-yl)methyl]piperidine
122 4-[(R)-naphthalen-2-yl(2H-1,2,3-triazol-2-yl)methyl]piperidine
123 4-[(S)-naphthalen-2-yl(1H-1,2,3-triazol-2-yl)methyl]piperidine
124 4-[(R)-naphthalen-2-yl(1H-1,2,3-triazol-2-yl)methyl]piperidine
125 4-[(S)-(3,4-dichlorophenyl)(2H-tetrazol-2-yl)methyl]piperidine
126 4-[(R)-(3,4-dichlorophenyl)(2H-tetrazol-2-yl)methyl]piperidine Compounds represented by structural Formula I and pharmaceutical acceptable salts thereof, e.g., the Example Compounds 1-126 above, may be prepared by techniques and procedures readily available to one of ordinary skill in the art. Further details of preparing compounds represented by structural Formula I and pharmaceutical acceptable salts thereof, e.g., the Example Compounds, may be found in found in U.S. Pat. Nos. 8,513,285 and 8,546,576, the entire contents of which are incorporated by reference herein.

In some embodiments, the compound may be selected from:

(3R)-3-[(R)-naphthalen-2-yl(2H-tetrazol-2-yl)methyl]piperidine;

(3S)-3-[(S)-naphthalen-2-yl(2H-tetrazol-2-yl)methyl]piperidine;

(3S)-3-[(S)-(5-methyl-2H-tetrazol-2-yl)(naphthalen-2-yl)methyl]piperidine;

(3R)-3-[(R)-(5-methyl-2H-tetrazol-2-yl)(naphthalen-2-yl)methyl]piperidine;

(3R)-3-[(R)-naphthalen-2-yl(2H-1,2,3-triazol-2-yl)methyl]piperidine;

(3S)-3-[(S)-naphthalen-2-yl(2H-1,2,3-triazol-2-yl)methyl]piperidine;
(3R)-3-[(R)-(3,4-dichlorophenyl)(2H-tetrazol-2-yl)methyl]piperidine;
(3S)-3-[(S)-(6-methoxynaphthalen-2-yl)(2H-tetrazol-2-yl)methyl]piperidine;
(3R)-3-[(R)-(6-chloronaphthalen-2-yl)(2H-tetrazol-2-yl)methyl]piperidine;
(3S)-3-[(S)-(6-chloronaphthalen-2-yl)(2H-tetrazol-2-yl)methyl]piperidine;
(3S)-3-[(S)-(6-fluoronaphthalen-2-yl)(2H-tetrazol-2-yl)methyl]piperidine;
2-{(S)-naphthalen-2-yl[(3S)-piperidin-3-yl]methyl}-2H-benzotriazole;
(3R)-3-[(R)-(6-fluoronaphthalen-2-yl)(2H-tetrazol-2-yl)methyl]piperidine;
(3S)-3-[(S)-(6-methylnaphthalen-2-yl)(2H-tetrazol-2-yl)methyl]piperidine; and
(3S)-3-[(S)-naphthalen-2-yl(1H-1,2,4-triazol-1-yl)methyl]piperidine.

In certain embodiments, the compound may be (3S)-3-[(S)-naphthalen-2-yl(2H-tetrazol-2-yl)methyl]piperidine, represented by the following formula:

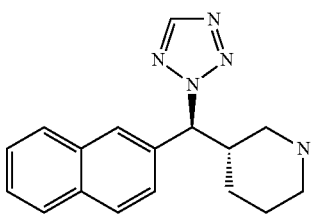

or a pharmaceutically acceptable salt thereof.

In another embodiment, a kit for treating a stress disorder in a subject in need of therapy is provided. The kit may include an effective amount of a compound represented by Formula I:

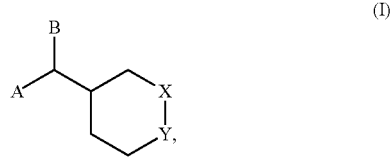

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl.

In structural Formula I, B may be a moiety represented by a structural formula selected from Group II:

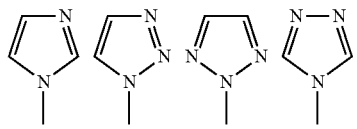

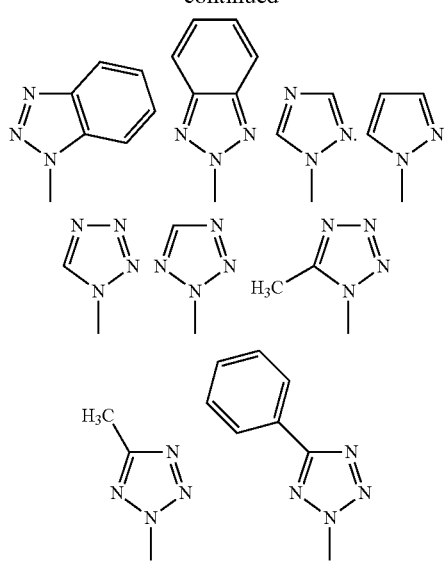

In structural Formula I, one of X and Y may be —$CH_2$— and the other may be —NR—. R may be H— or straight- or branched-chain $C_1$-$C_4$ alkyl.

The kit may also include instructions for administering an effective amount of the compound to the subject to treat the stress disorder in the subject. In various embodiments, In various embodiments, the stress disorder may include PTSD and/or ASD.

In several embodiments, the kit for treating a stress disorder may include any structure, substructure, moiety, group, substituent, Example Compound, stereoisomer, enantiomer, or pharmaceutically acceptable salt thereof for any compound or structural Formula described herein, such as for the compounds represented by structural Formula I. The stress disorder may include any aspect of stress disorders as described herein or in the DSM-IV or DSM-V as referred to herein.

In one embodiment, a kit for treating a substance use disorder in a subject in need of therapy is provided. The kit may include a compound represented by Formula I:

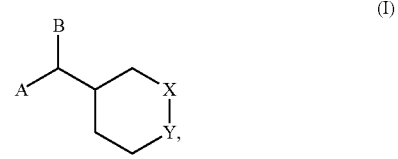

or a pharmaceutically acceptable salt thereof.

In structural Formula I, A may be selected from phenyl, naphthyl, benzothiophenyl, pyridyl, quinolyl, and isoquinolyl. A may be optionally substituted by one or more substituents selected from H—, halo, straight- or branched-chain $C_1$-$C_4$ alkyl, straight- or branched-chain $C_1$-$C_3$ alkoxy, nitro, cyano, trifluoromethyl, trifluoromethoxy, methanesulfonyl, phenyloxy, phenyl, and thienyl.

In structural Formula I, B may be a moiety represented by a structural formula selected from Group II:

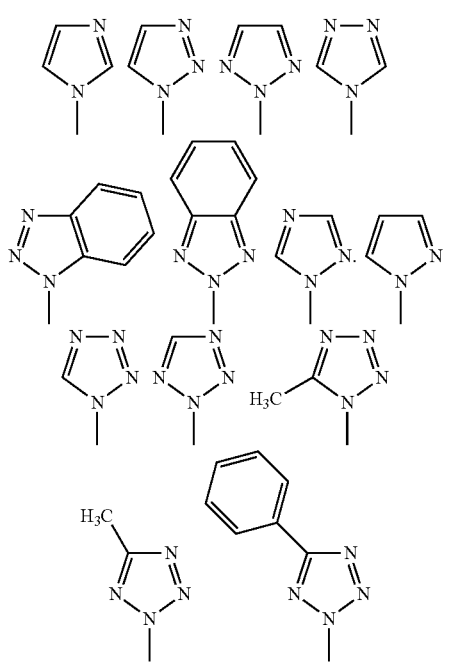

In structural Formula I, one of X and Y may be —CH$_2$— and the other may be —NR—. R may be H— or straight- or branched-chain C$_1$-C$_4$ alkyl.

In various embodiments, the kit for treating a substance use disorder may also include instructions for administering an effective amount of the compound to the subject to treat the substance use disorder in the subject. The substance use disorder may be one or more of an alcohol use disorder or a stimulant use disorder.

In several embodiments, the kit for treating a substance use disorder may include any structure, substructure, moiety, group, substituent, Example Compound, stereoisomer, enantiomer, or pharmaceutically acceptable salt thereof for any compound or structural Formula described herein, such as for the compounds represented by structural Formula I. The substance use disorder may include any aspect of substance use disorders described herein or in the DSM-IV or DSM-V as referred to herein.

In therapeutic use as agents for treatment of stress disorders and substance disorders, the compounds described herein, alone or in combination with a pharmaceutically acceptable carrier, may be administered to patients at a dosage of from 0.7 to about 7,000 mg per day. For a normal human adult with a body weight of approximately 70 kg, the administration amount may be translated into a daily dose of about 0.01 to about 100 mg per kg of body weight. The specific dosage employed may vary depending upon the requirements of the patient, the severity of patient's condition, and the activity of the compound. Optimum dosages for a particular situation may be clinically determined by one of ordinary skill of the art, such as a physician.

The compounds represented by structural Formula I or represented by a structural formula selected from Group III and IV, e.g., the Example Compounds, may be administered in any form or mode that makes the compound bioavailable in effective amounts, including oral, rectal, transdermal, subcutaneous, intravenous, intramuscular, or intranasal routes. In some embodiments, oral administration may be preferred, for example, because the compounds are reported to have good oral absorption. For oral administration, compounds represented by structural Formula I or represented by a structural formula selected from Group III and IV may be combined with a pharmaceutical carrier. The ratio of the carrier to the compound represented by structural Formula I or represented by a structural formula selected from Group III and IV is not critical to express the effects of the medicine on the central nervous system, and the effects can vary considerably depending on whether the composition is to be filled into capsules or formed into tablets. In tableting, various edible pharmaceutical carriers or a mixture thereof can be used. Suitable carriers, for example, are a mixture of lactose, dibasic calcium phosphate, and corn starch. Other pharmaceutically acceptable ingredients can be further added, including lubricants such as magnesium stearate.

EXAMPLES

The biological activity and potential therapeutic utility of the racemic or enantiomerically enriched compounds represented by structural Formula I or represented by a structural formula selected from Group III and IV and their pharmaceutically useful salts have been reported or established or may be assessed according to the following Examples.

Example 1

Serotonin Transporter Reuptake Inhibition Assay (Prior Art)

Serotonin transporter reuptake inhibition was assayed using the method described by Gu H. et al., J Biol Chem., 1994, 269, p 7214-7130, the entire contents of which are incorporated herein by reference. Recombinant HEK-293 cells with human serotonin transporter were plated. Test compounds were pre-incubated with cells (2×105/ml) in modified Tris-HEPES buffer at pH 7.1 for 20 min at 25° C. and were incubated for an additional 10 min after addition of 65 nM of [3H]Serotonin. Bound cells were filtered and counted to determine [3H]Serotonin uptake. Reduction of [3H]Serotonin uptake by 50 percent or more (≥50%) relative to 10 μM fluoxetine indicated significant inhibitory activity.

Example 2

Norepinephrine Transporter Reuptake Inhibition Assay (Prior Art)

Norepinephrine transporter reuptake inhibition may be assayed using the method described by Galli A. et al., J Exp Biol., 1995, 198, p 2197-2212, the entire contents of which are incorporated herein by reference. MDCK cells with stably expressed human recombinant norepinephrine transporter were plated. Test compounds were pre-incubated with cells (2×105/ml) in modified Tris-HEPES buffer at pH 7.1 for 20 min at 25° C. and were incubated for an additional 10 min after addition of 25 nM of [3H]Norepinephrine. A lysate was obtained from solubilized cells and the filtered lysate was counted to determine [3H]Norepinephrine uptake. Reduction of [3H]Norepinephrine uptake by 50 percent or more (≥50%) relative to 10 μM desipramine indicated significant inhibitory activity.

Example 3

Dopamine Transporter Reuptake Inhibition Assay (Prior Art)

Dopamine transporter reuptake inhibition was assayed using the following method modified from Pristupa Z. B. et al., Mol Pharmacol., 1994, p 125-135, the entire contents of which are incorporated herein by reference. CHO-K1 cells with human recombinant dopamine transporter were plated. Test compounds were pre-incubated with cells (4×105/ml) in modified Tris-HEPES buffer at pH 7.1 for 20 min at 25° C. and were incubated for additional 10 min after addition of 50 nm of [3H]Dopamine. A lysate was obtained from solubilized cells and counted to determine [3H]Dopamine uptake. Reduction of [3H]Dopamine uptake by 50 percent or more (≥50%) relative to 10 µM nomifensine indicated significant inhibitory activity.

FIG. 1 shows Table 1, which includes sample values reported for various Example Compounds described herein according to Examples 1, 2, and 3.

The data in Table 1 show that racemic or enantiomerically enriched 3 or 4-substituted piperidine derivatives have a significantly high inhibition potency with respect to serotonin, norepinephrine, and dopamine transporter reuptake.

Example 4

Forced Swimming Test in Mice (FST) (Prior Art)

The FST is a screen for drugs with potential anti-depressant activity based on an animal model's behavioral repertoire. An uncontrollable stress stimulus produces behavioral changes that are sensitive to anti-depressant treatment. Mice were intraperitoneally treated with an Example Compound, e.g., with an injection volume of 10 mg/kg. A group treated with 30% PEG400 served as a control group. 30 min following administration, mice may be individually forced to swim in a transparent glass vessel (e.g., 14 cm high, 11.5 cm in diameter) filled with 10 cm of water at 25° C. The total duration of immobility (seconds) may be measured during the last 4 min of a single 6 min test session. Mice were considered immobile when they made no further attempts to escape other than movements necessary to keep their heads above the water. The potent ability of the Example Compounds were determined as a percent value of reduction in the duration of immobility compared to the control group. Table 2 includes sample values reported for various Example Compounds described herein. The results of the FST in mice as noted in FIG. 2, Table 2, show that the Example Compounds are related to the treatment of depression.

Example 5

Marble Burying Test (Prior Art)

The Marble burying test is a screening tool employed to identify and rank anxiolytic drug candidates. Control mice naturally bury glass marbles in cage bedding. Administration of known anxiolytic compounds, such as Diazepam, reduces the number of marbles buried by the mice. Example Compounds in the marble burying test may be regarded as candidates for treating obsessive-compulsive disorder and/or anxiety.

Mice were intraperitoneally treated with an Example Compound dissolved in 30% PEG400 with an injection volume of 10 ml/kg. A control group may be treated with only 30% PEG400. 30 min after the treatment, the animals were individually placed in a conventional polycarbonate housing cage with an open top, all located within a quiet room. Each cage included ⅛ inch corn bedding in a 5 cm deep layer. Twenty-four clean glass marbles (e.g., 15 mm diameter) were evenly spaced in four rows of six on top of the bedding. Each mouse was left in the cage for 30 min and the number of marbles buried (buried more than ½ or ⅔) was counted. The potent ability of the compounds was determined as a percent value of reduction in the number of marbles buried compared to the control group. Table 4 includes sample values reported for various Example Compounds described herein. The results of the Marble burying test in mice as noted in FIG. 3, Table 3 show that the Example Compounds are related to the treatment of anxiety and/or Obsessive/Compulsive disorder.

Example 6

Acetic Acid Induced Writhing Test (Writhing Test) (Prior Art)

The Writhing Test is a well-established nociceptive test using a chemical stimulus. Although several animal models of nociceptive tests have been developed to examine and compare the anti-nociceptive effects of different drugs, the anti-nociceptive effects of antidepressants appear to be test-dependent. The Writhing Test is known to be more sensitive to anti-depressants than other tests using thermal, mechanical, or electrical stimuli. Mice were subcutaneously treated with an Example Compound with an injection volume of 10 ml/kg. A control group was treated with 30% PEG400 or saline. Thirty minutes later, the mice were intraperitoneally treated with 0.8% (v/v) acetic acid. Each mouse was placed in a cage for individual observation. The writhing numbers for 10 min were counted. Each writhe is operationally defined as a contraction of the abdomen followed by stretching of the hind limbs. The potent ability of the compounds were determined as a percent value of reduction in the number of writhing compared to the control group. The results noted in FIG. 4, Table 4 show that the Example Compounds are related to the treatment of pain.

Example 7

The Compounds of the Method have Similar $IC_{50}$ Values for Human SERT, NET, and DAT Proteins FIG. 5, Table 5 shows $IC_{50}$ values at the recombinant human serotonin transporter protein (SERT), recombinant human norepinephrine transporter protein (NET), and, and recombinant human dopamine transporter protein (DAT) for the hydrochloride salt of Example Compound 2 ((3S)-3-[(S)-naphthalen-2-yl(2H-tetrazol-2-yl)methyl]piperidine.HCl) and two structurally different triple monoamine uptake inhibitors, amitifadine.HCl and DOV 102,677.HCl:

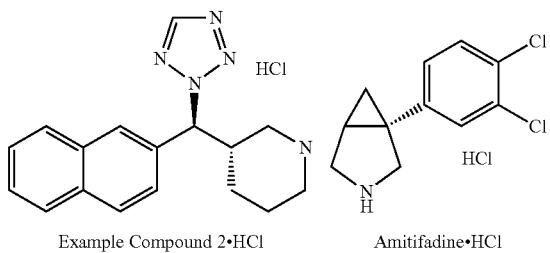

Example Compound 2•HCl     Amitifadine•HCl

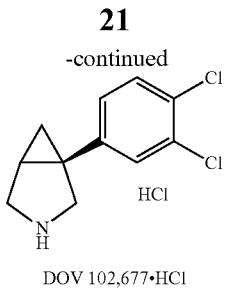

DOV 102,677·HCl

Example Compound 2 is substantially different in structure compared to amitifadine and DOV 102,677. Amitifadine and DOV 102,677 are enantiomers and differ only in the stereochemistry of the cyclopropyl pyrrolidine carbon to which the dichlorophenyl group is bonded. In addition to the structural differences, the compounds differ greatly in their $IC_{50}$ binding profiles at the three corresponding monoamine transporter proteins. The $IC_{50}$ binding profiles were measured for each of the compounds in Table 5 by competitive inhibition assays using recombinant human serotonin transporter protein, recombinant human norepinephrine transporter protein, and recombinant human dopamine transporter protein Compounds were screened at a range of concentrations and were fit to a curve to determine $IC_{50}$ values, the concentration at which 50% inhibition occurs.

Example 8

Monoamine Uptake Inhibition in Rat Synaptosomes and Rat Prefrontal Cortex

Figure 6B:
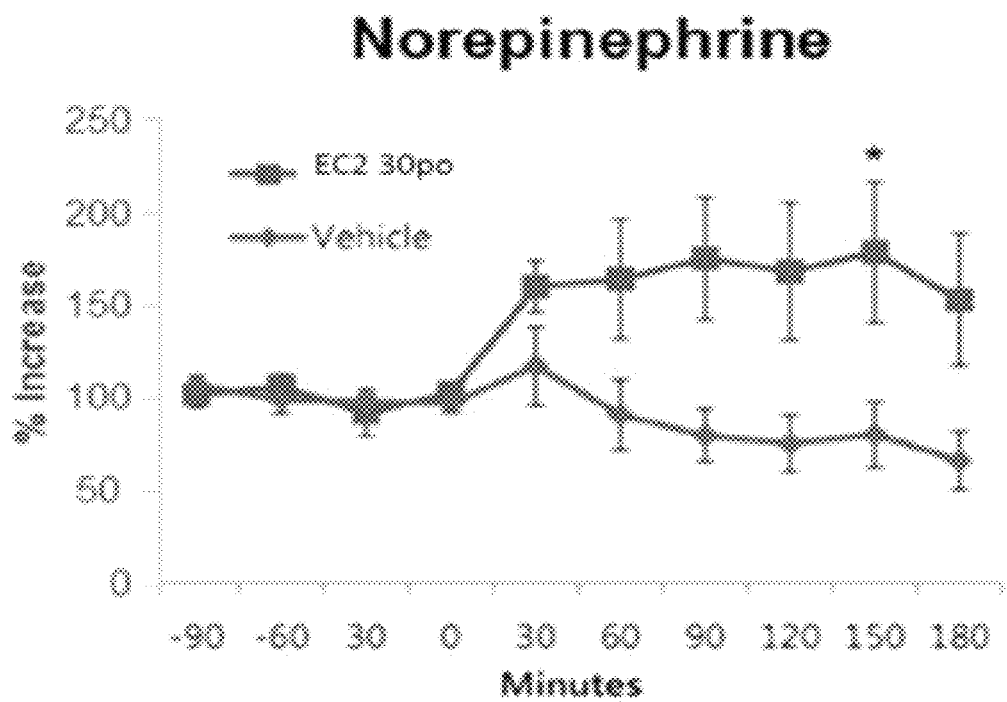
Figure 6C:
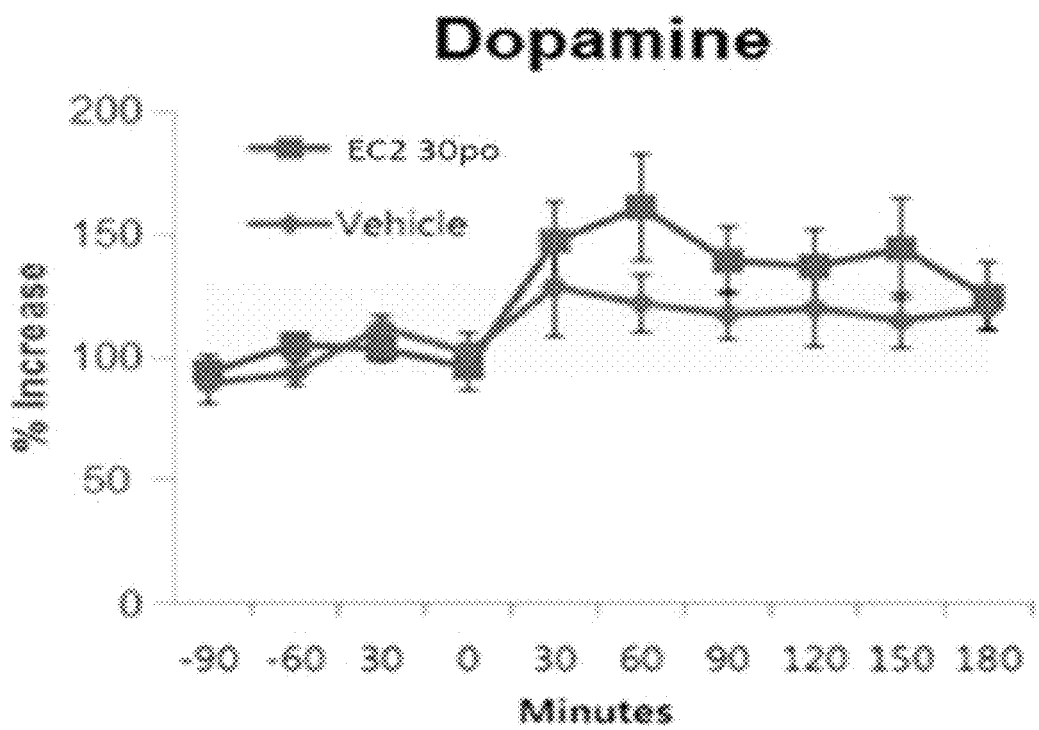

Example Compound 2 inhibited monoamine uptake into rat synaptosomes at serotonin, norepinephrine, and dopamine transporters at measured $IC_{50}$ values of 37 nM, 65 nM, and 74 nM, respectively. Separately, FIGS. 6A, 6B, and 6C are graphs showing the effect of oral treatment with Example Compound 2 on synaptic levels of serotonin, norepinephrine, and dopamine, respectively, in rat prefrontal cortex. Example Compound 2 shows clear effects on all three monoamines, with greater effects on levels of serotonin and norepinephrine as compared to dopamine, as was observed in the rat synaptosomal preparation.

Example 9

Example Compound 2 Reduces Binge Alcohol Drinking in Rats

The effect of treatment with Example Compound 2 on binge alcohol drinking in alcohol preferring P rats was investigated. Example Compound 2 was mixed immediately before the experimental test sessions in a volume of 1 ml/kg in deionized water. This composition of Example Compound 2 was given by oral gavage 25 min prior to all experimental sessions. Animals were habituated to the gavage procedures by administering deionized water alone over a number of experimental sessions.

Binge Drinking.

Animals were tested in 30 individual standard operant chambers (Coulbourn Instruments, Inc., Lehigh Valley, Pa.). The operant apparatus contained two levers, two dipper manipulanda, a cue light over each lever, and a house light. The dipper cup delivered either 10% (v/v) alcohol or 1% (w/v) sucrose reinforcers in a volume of 0.1 ml. To initiate excessive "binge" alcohol drinking, rats were adapted to a 12 h:12 h light/dark cycle which began at 4:30 pm (lights off) and lasted to 4:30 am (lights on). Rats were trained to orally self-administer EtOH for daily 30 min sessions under an FR1 schedule employing the sucrose fading technique. After a period of stabilization, the response requirement was then increased to an FR4 schedule. Responding was considered stable when responses were within ±20% of the average responses for five consecutive days, which took approximately 8 days. During the stabilization procedures, the animals were never deprived of food or fluid. Other cohorts of rats were given a 1% (w/v) concentration of sucrose and trained in an identical manner under the FR1, then FR4, schedule. Following stabilization on the FR4 schedule for EtOH/sucrose, in "binge" sessions the rats were given access to 10% (v/v) alcohol, or 1% sucrose (w/v) on both the left and right levers. Self-administration was assessed in 3×30 min FR4 operant sessions spaced 1 h apart during the dark cycle. Rats were placed in the home cage between assessment sessions. Food and water were available ad libitum.

Results.

Figure 7B:
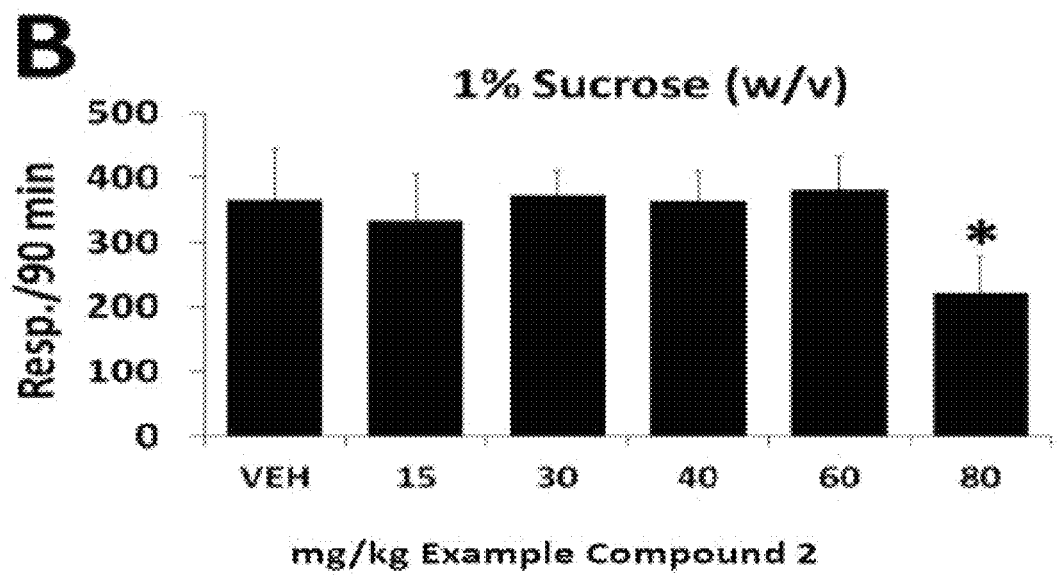

Oral administration of 15 mg/kg (N=5), 30 mg/kg (N=5), 40 mg/kg (N=4), 60 mg/kg (N=5), or 80 mg/kg (N=4) of Example Compound 2 in P rats significantly reduced binge operant responding for alcohol (total N=28) (FIG. 7A; $F_{(5.22)}$=7.056; p<0.001) but not for sucrose (total N 30) (FIG. 7B; $F_{(5.24)}$=1.033; p=0.421).

Newman-Keuls post hoc analyses confirmed the reduction of operant responding by all doses of Example Compound 2 (p≤0.05). Oral administration of Example Compound 2 failed to significantly reduce binge sucrose responding in P rats (p>0.05), except for the 80 mg/kg dose.
* p≤0.05 compared with vehicle-treated P rats (N=5).

Example 10

Example Compound 2 is Safe, Exhibiting Tolerable Off-Target Binding

Receptor Binding Studies.

In a series of binding studies, Example Compound 2 (10 µM) was tested at 56 receptors, channels, and transporters, including 5-HT1A, 5-HT1B, 5-HT2A, 5-HT2B, 5-HT3,5-HT4,5-HT5A, 5-HT6, D2, D4, D8, sigma σ1, σ2, kainate, AMPA, imidazoline 12, muscarinic M1, M2, H1, H2, adenosine transporter, choline transporter, GABA transporter, NK1, NK2, NK3, Y1, Y2, and NT. There was no significant binding at any of these sites, except σ1 (74% inhibition at 10 uM) and 5-HT2B (56% inhibition at 10 uM). Antagonist activity at 5-HT2B receptor is important because agonist activity at this receptor is thought to contribute to cardiac valvulopathy produced by fenfluramine; Example Compound 2 has antagonist activity indicating that it will not cause valvulopathy. Binding at σ1 is not problematic, as SSRIs are known to have similar activities.

Example 11

Example Compound 2 has Low Abuse Potential

As shown in FIG. 8, Example Compound 2 is not self-administered in rats in doses up to 10 mg/kg/infusion, a very sensitive indicator of abuse potential. Cocaine served as the positive control. Example Compound 2 does not cause increases in locomotor activity, a screening test for stimulant-like effects. Similar to the triple uptake inhibitors tesofensine (NS2330) and amitifadine (EB-1010, DOV 21,947), Example Compound 2 does not produce positive subjective effects in humans, a predictor of abuse potential. Thus Example Compound 2 is very unlikely to have abuse potential.

Example 12

Example Compound 2 has Good Metabolic Stability and Low Toxicity

In other studies, Example Compound 2 was shown to have high metabolic stability in human liver microsomes and hepatocytes. The PK parameters of Example Compound 2 are favorable in animal studies $T_{1/2}$ (hr): mouse (1.9), rat (3.7), dog (2.0), and monkey (5.8). It is mainly excreted in feces by rodents. It has good brain penetration in the rat with an AUC ratio (brain/plasma) of 0.45 after oral dosing. It does not accumulate in any tissue.

Example Compound 2 does not inhibit major CYP450 isoenzymes—1A2, 2C8, 2C9, 2C19, 3A4 but it does inhibit 2D6 at 10 uM. It does not induce CYP 1A2, 2B6 or 3A4. Clinical studies (described below) suggest that Example Compound 2 is metabolized by CYP2D6.

Standard preclinical testing suggests a good safety profile, with moderate hERG channel inhibition accompanied by offsetting inhibition of other ion channels. Confirming the absence of cardiac toxicity, Example Compound 2 had no effects on ECG or QT in telemetry studies conducted in dogs at doses up to 20 mg/kg. Standard genotoxicity testing (AMES, micronucleus, and mouse lymphoma chromosome aberration) was negative. Chronic (13 week) testing showed no adverse effects level (NOAEL) of 60 mg/kg in rats and 6 mg/kg in dogs. The Irwin test for neurotoxicity and respiratory testing in rats were both negative up to 90 mg/kg. There were no adverse Example Compound 2-related macroscopic, organ weight, and microscopic evaluations. Teratogenicity study (segment II) in rats demonstrated that the NOAEL maternal toxicity was 30 mg/kg/day, the NOAEL fetal viability was 90 mg/kg/day, the NOAEL fetal growth was 30 mg/kg/day, and the NOAEL fetal development was 90 mg/kg/day. Reproductive toxicity testing (segment I and segment II) and 6 month repeated dose toxicity testing remain to be completed, as does a food interaction study. These can be conducted later should the proposed research support further development of Example Compound 2.

ADM&E studies demonstrated that Example Compound 2 was stable, had modest protein binding, and had oral bioavailability ranging from 10% in monkeys to 45% in dogs. Example Compound 2 was widely distributed across most tissues in rat after oral administration, without significant accumulation in any tissue. The brain/plasma AUC ratio in rats was 0.45, and the elimination half-life in brain was 12.6 h, compared to 5.0 h in plasma.

Example 13

Example Compound 2 is Safe in Single Ascending Dose Study in Healthy Volunteers

A single ascending dose, double-blind, placebo controlled study enrolled 50 participants divided into 10 per dosing group. In each group of 10 volunteers, 7 received active medication and 3 received placebo. The doses tested were 10, 25, 75, 150, and 300 mg. Plasma concentration was proportional to dose. Across most doses, the elimination half-life was ~10 h. Example Compound 2 was safe at doses up to 300 mg. The primary adverse effects were nausea, dizziness, and headache, increasing in prevalence at doses of 75 mg and higher.

Example 14

Example Compound 2 is Safe in Multiple Ascending Dose Study in Healthy Volunteers A multiple ascending dose study in healthy volunteers evaluated safety and pharmacokinetics of daily doses of Example Compound 2 administered for up to 11 days. This double-blind, placebo controlled study enrolled 50 participants divided into 10 per dosing group. In each group of 10, 7 received active medication and 3 received placebo to maintain the blind. The doses tested were 25 mg BID, 75 mg QD, 50 mg BID, 75 mg BID, and 100 mg BID. Pharmacokinetic results are shown in FIG. 9, Table 6.

Across all doses, plasma concentration was proportional to dose. For most doses, the elimination half-life during chronic treatment was ~6 h. Genotype analysis demonstrated that CYP2D6 was primarily responsible for metabolism of Example Compound 2, with 3A4 playing a role at doses above 100 mg/d (CYP 2D6 poor metabolizers are excluded from Table 6).

Adverse event data are shown in FIG. 10, Table 7. The primary adverse events were nausea, vomiting and headache. Example Compound 2 is a potent inhibitor of 5-HT reuptake, and this potentially accounts for treatment-associated nausea, as SSRIs as a group also cause nausea, especially soon after initiating treatment. SSRI-induced nausea may decrease over time, and nausea is not a dose-limiting factor for SSRIs in the treatment of depression. Other common side effects (>10% of participants) were dizziness, headache, anxiety, and sleep disorder.

Example Compound 2 had no effects on vital signs or on QTc. This is important because two triple uptake inhibitors under development reportedly produce dose-dependent increases in blood pressure.

Prophetic Example 15

Example Compound 2 Will Attenuate the Behavioral Effects of Alcohol in Multiphase Human Laboratory and Clinical Trials This parallel group, placebo-controlled experimental protocol will assess the effects of Example Compound 2 (50 and 75 mg BID) compared to placebo on the effects produced by alcohol in 20 non-treatment-seeking alcohol-dependent volunteers. Dosing will be started at 50 mg BID and increased to 75 mg BID after half of the participants complete the study. Medications will be stored and dispensed daily. Study physicians will be present daily and emergency physician coverage and a code team will be available at all times. The inclusion/exclusion criteria below pertain to both the human laboratory study and the clinical trial.

Inclusion Criteria

In order to participate in the study, participants will:
1. Be English speakers who are 21-55 years of age;
2. For the human laboratory study volunteers will not be seeking treatment for alcohol dependence;
3. For the clinical trial volunteers will be seeking treatment for alcohol dependence;
4. Must carry CYP2D6 *1 or *2 alleles as these are associated with normal enzyme activity phenotype;

5. Currently drinking heavily (>5 standard units for male, >4 for female) on at least 30% of days in the last 30 days;
6. Meet DSM-IV TR criteria for alcohol dependence; participants may or may not meet criteria for nicotine dependence (*Diagnostic and Statistical Manual of Mental Disorders IV* (Text Revision) (DSM-IV-TR) (5th ed., American Psychiatric Association, Washington, D.C., 2000), the entire contents of which are incorporated herein by reference);
7. Subjects will score <10 on the revised clinical institute withdrawal assessment for alcohol scale (CIWA-Ar) assessed in the context of an undetectable (0%) blood alcohol level to demonstrate that they do not need medical detoxification;
8. Have hematology and chemistry laboratory tests that are within normal (+/−10%) limits with the following exceptions: a) liver function tests (total bilirubin, ALT, AST, and alkaline phosphatase)≤3× the upper limit of normal, and b) kidney function tests (creatinine and BUN) within normal limits;
9. Have a baseline ECG that demonstrates clinically normal sinus rhythm, clinically normal conduction, normal QTc, and no clinically significant arrhythmias;
10. Have a medical history and brief physical examination demonstrating no clinically significant contraindications for study participation, in the judgment of the admitting physician and the principal investigator (PI).

Exclusion Criteria

In order to participate in the study, participants will not:
1. Meet DSM IV TR criteria for dependence on drugs other than alcohol or nicotine;
2. Be pregnant or nursing. Other females will either be unable to conceive (i.e., surgically sterilized, sterile, or post-menopausal) or will be using a reliable form of contraception (e.g., abstinence, birth control pills, intrauterine device, condoms, or spermicide). All females will provide negative pregnancy urine tests before study entry, upon hospital admission, and at the end of study participation;
3. Be taking antidepressants or any medication that could interact with EC2 or alter the effects of alcohol;
4. Have any history or evidence suggestive of seizure disorder or brain injury;
5. Have neurological or psychiatric disorders, such as: psychosis, bipolar illness or major depression; organic brain disease or dementia assessed by clinical interview; history of any psychiatric disorder which would require ongoing treatment or which would make study compliance difficult; history of suicide attempts within the past year and/or current suicidal ideation/plan;
6. Have evidence of untreated or unstable medical illness including: neuroendocrine, autoimmune, renal, hepatic, or active infectious disease;
7. Have a history of major alcohol-related medical complications requiring hospitalization (i.e. hepatitis or pancreatitis);
8. Have contraindication(s) to take the study medication such as renal or hepatic impairment, or history of seizures;
9. Be more than thirty days abstinence from alcohol during the three months prior to enrollment.

Criteria for Discontinuation of Dose Adjustment:

Inability to comply with study procedures or meet discontinuation criteria due to exaggerated response to alcohol in the human laboratory study, described below. The dose will be adjusted if Example Compound 2 treatment is associated with nausea that necessitates medication discontinuation.

Stopping Rules.

In the human laboratory study, alcohol will not be administered if vital signs are outside of acceptable ranges or if there are significant Example Compound 2 side-effects (e.g. severe nausea) that affect an individual's ability to participate in the protocol. The stopping criteria for further participation of a given participant includes symptomatic dizziness leading to syncope or fall and development of exaggerated response to alcohol more than once. The clinical trial (phase II) will be halted if the pattern of adverse events indicates that the selected dose of Example Compound 2 is inappropriate. The study may be restarted using a different Example Compound 2 dose if appropriate.

Study Procedures (Human Laboratory Study)

After completing screening procedures as outpatients, participants (n=20) will arrive at the research ward on the day of admission where they will undergo daily breath alcohol and urinary drug screen to ensure drug abstinence. Participants will then be randomly assigned to receive Example Compound 2 50 mg BID or placebo bid. After half the participants have completed the study the dose will be increased to 75 mg BID. Twice each day, 1 hour after study medication dosing, subjective effect ratings, administer symptom checklists, and conduct cognitive and psychomotor assessments will be collected. On day 4 blood will be collected for measurement of peak and trough plasma concentrations on Example Compound 2 and participants will receive doses of alcohol and of a placebo solution, with the doses separated by several hours. The order will be counterbalanced across participants. The alcohol beverage will be prepared in a volume of 450 ml for a 70 kg individual and adjusted for body weight by varying the volume. Alcohol will be administered in a concentration of 16% alcohol (Everclear, St. Louis, Mo.) by volume in grape Kool-Aid (Kraft Foods, Northfield, Ill.). Participants will be allowed 15 minutes to consume the beverage. Studies show that the dose of alcohol selected (0.8 g/kg) produces stimulant-like effects and rating of drug "liking". Placebo will contain 1% alcohol to mask the condition with regard to taste. Physiological effects, subjective effects and breath alcohol levels (BAL) will be obtained prior to and after consuming the alcoholic beverage every 30 min for 2 hours. A wide variety of subjective effects data will be collected prior to and following alcohol/placebo administration. This may provide detection of common side effects and may determine if alcohol administration exacerbates the side effects of Example Compound 2, and vice versa.

Assessments (Human Laboratory Study)

To monitor safety, during screening and daily medical history and physical exam, concomitant medication use, mental status exam, height, body weight, vital signs (heart rate, blood pressure, respiratory rate, and temperature), and 12 lead ECG will be assessed. Clinical laboratory tests (including CBC, electrolytes, comprehensive metabolic panel, urinalysis, urine toxicology tests for illicit drug use, and urine pregnancy testing for females with reproductive capacity will be assessed prior to admission and repeated on day 4.

Because nausea and dizziness are the most common side effects reported after Example Compound 2 administration, a target symptom checklist will be used for Example Compound 2 to measure nausea and dizziness (rated from 0 to 4, "not at all" to "extremely"). Alcohol alone produces characteristic cognitive and psychomotor effects, and these will be monitored using standard neuropsychological tests: the Digit-Symbol Substitution Test (DSST), the Biphasic Alcohol Effects Scale (BAES), and the Morphine-Benzedrine Groups (MGB) scale of the Addiction Research Center Inventory (ARCI). The DSST has been used frequently to measure sedative impairment of perceptual-motor function. This test has been shown to be sensitive to dose-related impairments produced by alcohol. The BAES is a 14-item adjective rating scale (scored 0-10) which has been validated to measure stimulant effects of alcohol during the ascending limb of the blood alcohol curve and sedative effects during the descending limb of the curve. The MGB scale of the ARCI also reflects stimulant effects. A measure of motor balance will be included, assessed as duration of time the participant is able to stand on one foot, to determine whether Example Compound 2 treatment exacerbates alcohol's effect on balance. This measure is similar to body sway, a standard assessment of alcohol effects.

Example 16

Example Compound 2 Attenuates the Behavioral Effects of Methamphetamine in Rats

Example Compound 2 was tested in combination with methamphetamine (METH) and alcohol. It was discovered that Example Compound 2 attenuated the behavioral effects of these addictive substances in rats.

Adult male Sprague-Dawley rats (n=5-6/group, Harlan Sprague-Dawley Inc., Indianapolis, Ind., USA) were used in this study. Rats were housed three per cage in polypropylene cages in a temperature- and humidity-controlled room maintained on a 12:12 light/dark cycle (lights on at 7:00). Food and water were available ad libitum. Protocols were approved by the Baylor College of Medicine Institutional Animal Care and Use Committee and followed the "Principles of Laboratory Animal Care" (NIH publication No. 85-23, revised 1996). Facilities were accredited by the American Association of Laboratory Animal Care.

The TruScan photobeam activity system (Coulbourn Instruments, Allentown, Pa., USA) was used to measure horizontal and vertical distance traveled in centimeters (cm). This system includes a clear arena (16"L×16"W×15.5"D) that had two sets of infrared sensors with one located at floor level and the other 2.5" above floor level. Data from beam breaks were tabulated and analyzed by a PC computer and using a Coulbourn Instruments software system (TruScan 2.03).

METH HCl (National Institute on Drug Abuse, Research Triangle Park, N.C., USA) and Example Compound 2 (EC2) (SK Biopharmaceuticals, South Korea) were prepared in sterile saline and administered IP in a volume of 1 mg/mL by body weight (kg). Drug solutions were prepared fresh daily. To test the effects of EC2 on METH locomotor activation, groups of rats were administered vehicle (saline), METH (1 mg/kg), EC2 (30.0 mg/kg) and EC2+METH. Pretreatment time was 30 min for EC2.

Rats were randomly divided into groups then administered saline, and habituated to the apparatus for 60 min daily until baseline accumulative measures did not significantly differ. Testing began on the next day (day 1) and continued for the next five days. Rats were administered drugs according to group and immediately placed in the activity chambers for 60 min.

Data were first assessed with normality (Shapiro-Wilk) and equal variance tests. Distance traveled (cm), which reflects ambulatory activity, and vertical distance (cm) were the primary dependent variables analyzed. Habituation locomotor activity (baseline habituation, HAB) was assessed using a One-Way ANOVA with treatment as the main factor, and Student-Newman-Keuls Method was used for post-hoc comparisons. Data that did not pass normality or equal variance tests were analyzed with Kruskal-Wallis One-Way ANOVA on Ranks with treatment as the main factor. Dunn's method was used for post-hoc multiple comparisons between groups. Data are presented as mean±SEM and significant p values set at <0.05.

Figure 11A:
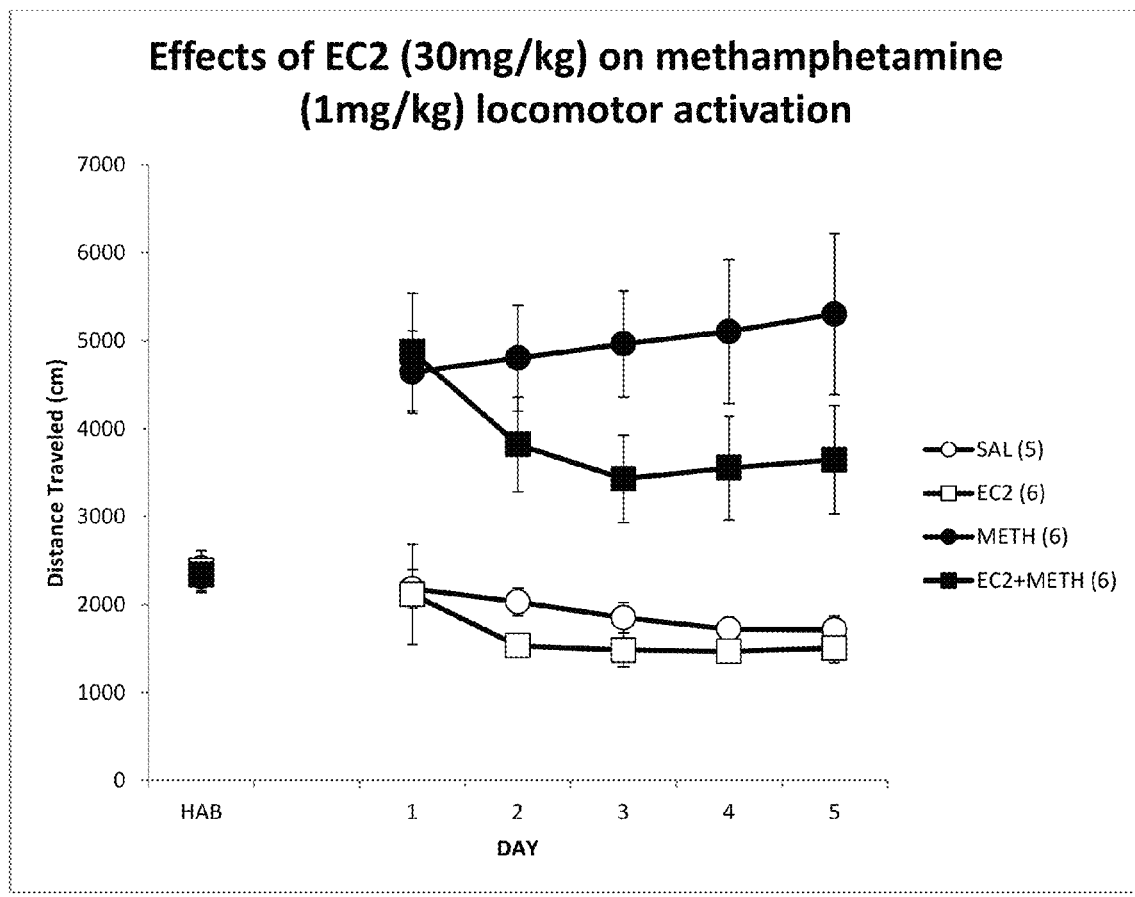
FIGS. 11A and 11B are graphs showing the effect on locomotor activation for combined administration of methamphetamine and Example Compound 2 in baseline and vertical distance traveled, respectively, according to Example 16.
Figure 11B:
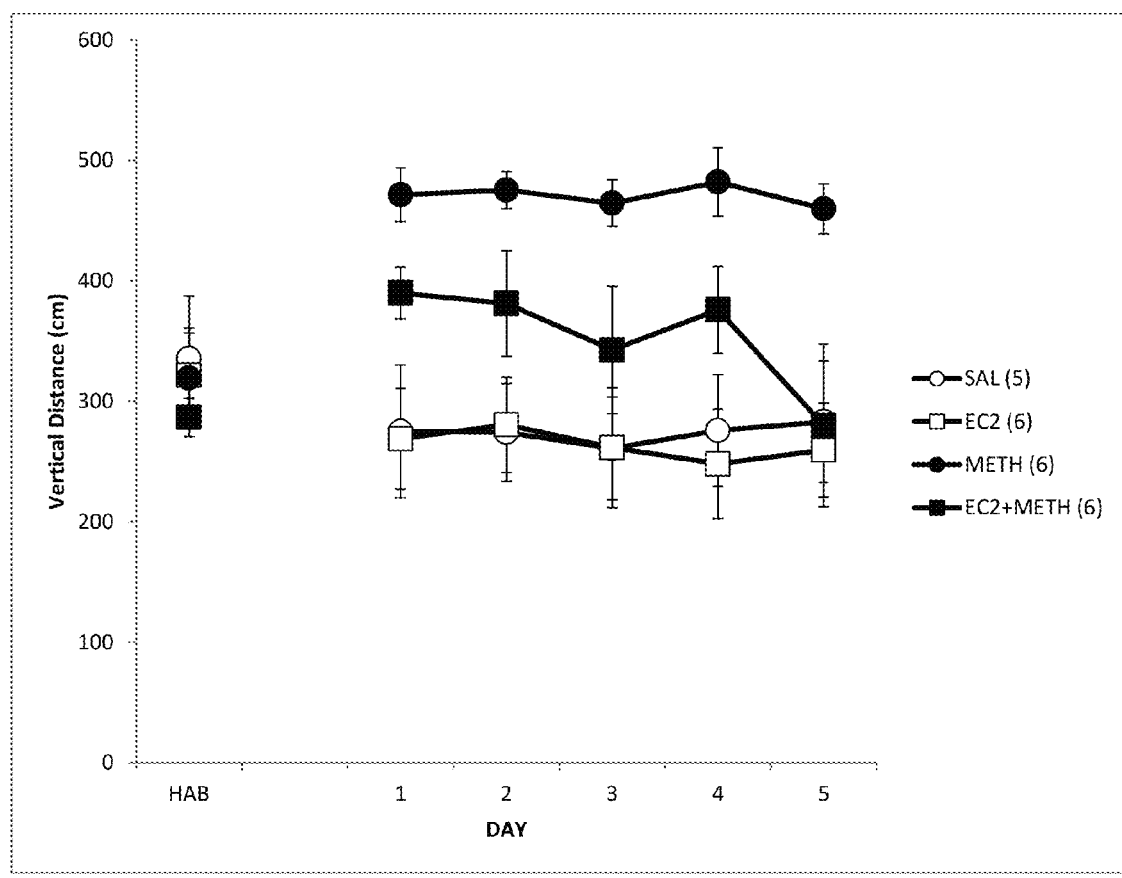
Figure 12A:
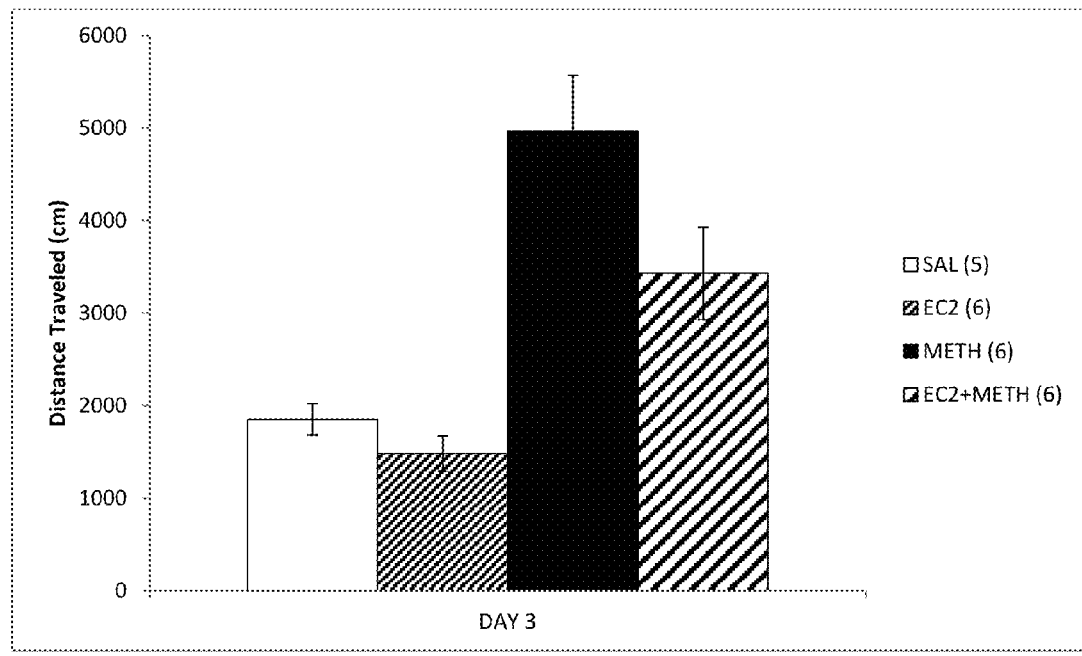
FIGS. 12A and 12B are graphs showing the effect on locomotor activation for combined administration of methamphetamine and Example Compound 2 in baseline and vertical distance traveled, respectively, at day 5, according to Example 17.
Figure 12B:
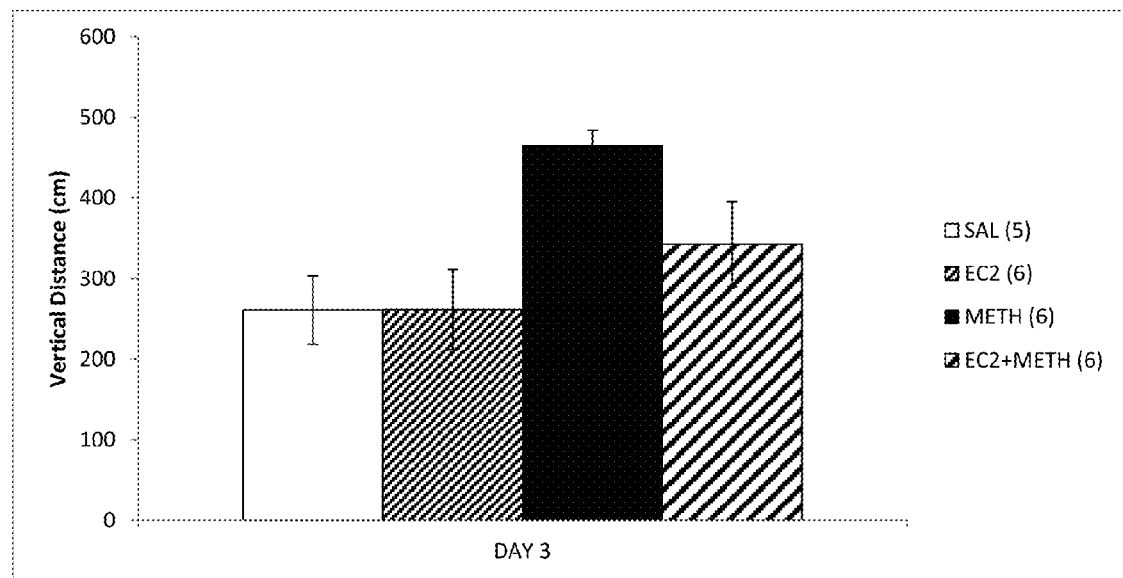

ANOVA showed no difference between treatment groups on baseline distance traveled ($F(3.22)=0.040$, $p=0.098$, FIG. 11A) or vertical distance ($F(3.22)=0.313 p=0.815$, FIG. 11B). A significant main effect was found for distance traveled over the 5 days between treatment groups ($H=73.244$; $p<0.001$; FIG. 11A). Multiple comparisons indicated significant differences in distance traveled between all groups except METH alone vs. EC2+METH and SALINE vs. EC2 alone ($p>0.05$). ANOVA also indicated a main effect between treatment groups for vertical distance ($H=60.726$; $p<0.001$). Multiple comparisons showed differences between all groups except SALINE vs. EC2+METH and SALINE vs. EC2 alone ($p>0.05$).

Treatment with EC2 significantly attenuated METH-induced locomotor activation, an effect more apparent on vertical distance measures. Treatment with EC2 alone did not differ from saline on both activity measures. This suggests that the effects of EC2 were specific to METH's behavioral effects and not due to gross disruptions in motor activity (e.g. stereotypy).

Example 17

Example Compound 2 Attenuates the Behavioral Effects of Methamphetamine in Rats at Day 5

The preceding example was continued for 5 days. Data from day 5 passed normality and equal variance tests and were analyzed with One-Way ANOVA with treatment as the main factor. Post-hoc pairwise multiple comparison procedures were performed using Student-Newman Keuls Method was used to determine group differences. Data are presented as mean±SEM and significant p values set at <0.05.

A significant main effect was found for distance traveled on day 5 between treatment groups ($F(3.22)=10.251$; $p<0.001$, FIG. 12A). Multiple comparisons indicated significant differences in distance traveled between all groups except SALINE vs. EC2(EC2) alone ($p>0.05$). ANOVA also indicated a main effect between treatment groups for vertical distance ($F(3.22)=4.559$; $p=0.014$, FIG. 12B). Multiple comparisons showed significant differences between METH alone and all other treatment groups ($P<0.05$).

Treatment with EC2 significantly attenuated METH-induced locomotor activation following 5 days of administration. This effect was more apparent on vertical distance since METH in combination with EC2 did not differ from saline nor EC2 alone. Importantly, treatment with EC2 alone did not differ from saline on both activity measures. This suggests that the effects of EC2 were specific to blockade of METH's behavioral effects and not due to gross disruptions in motor activity (e.g. stereotypy).

Prophetic Example 18

Example Compound 2 Will Attenuate the Behavioral Effects of Methamphetamine in Multiphase Human Laboratory and Clinical Trials Phase 1 research will identify doses of EC2 that are safe when combined with MA. The maximum tolerated dose (MTD) of EC2 will be identified when administered with up to 50 MA mg IV in otherwise healthy non-treatment-seeking MA-dependent volunteers. Phase 2 research will evaluate the efficacy of EC2 as a treatment for MA dependence. Phase 2 human laboratory research will evaluate the efficacy of several doses of EC2 for reducing the subjective and reinforcing effects of MA in non-treatment-seeking volunteers. Results from these safety and potential efficacy studies will guide dose selection for an outpatient clinical trial that will evaluate the impact of treatment with the selected dose of EC2 on MA use among treatment-seeking MA-dependent volunteers.

These studies will use double-blind, placebo-controlled experimental designs. Human pharmacokinetic studies indicate that EC2 has an elimination half-life of approximately 7 hours, allowing twice daily dosing.

Human Laboratory Study 1 will use evaluate the effects of treatment with ascending doses of EC2 using the Bayesian Continual Reassessment Method (CRM) in 6 cohorts of 4 participants (24 participants in total). In each cohort 3 participants will receive EC2 and 1 will receive placebo to maintain the blind. The Bayesian Continual Reassessment Method is recommended by the FDA for testing medications with dose-dependent efficacy and toxicity, such as cancer chemotherapeutic agents EC2 may display dose-dependent efficacy and side effects (toxicity).

Upon study entry, prior to receiving study medication, participants will receive ascending doses of 20 and 30 mg MA (total dose 50 mg) IV with a dose of saline placebo interspersed to maintain the blind. Dosing will be at 30 minute intervals. These pre-randomization MA doses will allow exclusion of participants with atypical responses to MA alone (some participants may not detect these MA doses and others may respond too robustly) and will serve as a baseline from which to determine the impact of EC2 treatment on effects produced by MA. On day 5 of treatment with the target dose of study medication participants will again receive ascending doses of 20 and 30 mg MA IV with a dose of saline placebo interspersed. Safety and tolerability of MA administration during treatment with EC2 will be based on blood pressure measurements and side effects assessment. Blood pressure is a focus because both EC2 and MA enhance NE signaling, which may raise blood pressure. Depending on those outcomes, the next cohort will receive the next higher dose of EC2, a lower dose (if there is evidence for toxicity), or the same dose (if the outcome is equivocal). The dose of EC2 will be started at 25 mg BID and titrated to the target dose. The evaluation will regard 25 mg BID, 50 mg BID, 75 mg BID and 100 mg bid.

MA will produce increases in blood pressure together with usual psychostimulant effects when administered alone. Blood pressure increases will remain within a safe range. The effects of MA observed prior to treatment will be compared with study medication to effects observed during treatment with study medication. "Toxicity" will be defined as a ≥10% sustained increase in systolic or diastolic blood pressure (BP) or the presence of unacceptable side-effects when EC2 is administered together with MA. Rates of toxicity (coded present or absent) will be used to update a dose-toxicity function which provides estimates of the expected probability of toxicity at each dose. The target probability of toxicity (p(tox)) selected at the MTD will be p(tox)=0.10 (10%).

The model for dose-toxicity relation is: $p(tox) = pdose^{(exp(\alpha))}$ where p(tox) is the probability of toxicity, pdose is the prior probability of toxicity at the dose level $\alpha=0$. For EC2 doses of 25 mg BID, 50 mg BID, 75 mg BID and 100 mg bid, the prior probabilities of toxicity with increasing dose are estimated to be 0.01, 0.01, 0.02, 0.05, 0.10, and 0.20, respectively. These estimates are arbitrary and will be updated based on observed data as each cohort of participants completes the study. As successive cohorts enter the study, data on the number of participants experiencing a toxicity may allow the re-estimation of the posterior distribution of a which may permit recalculation of p(tox) at each dose. The dose with the closest predicted p(tox) to the target p(tox) is the next dose selected for administration (within the constraints of the safety rules stated below). The study will use a double-blind placebo controlled design.

The following stopping rules will be used: if results indicate that the lowest dose has ≥0.20 probability of exceeding a p(tox)=0.05 (i.e. p(ptox)>0.05)=0.20) then the trial will stop and the dose range will be re-evaluated and shifted downward. Successive cohorts will not be escalated more than one dose level at a time. After 6 cohorts of 4 participants have complete human laboratory study 1, a good estimate of the maximum tolerated dose of EC2 when administered together with up to 50 mg IV MA will be obtained. These results will guide dose selection in studies conduction in Phase II of the project.

Human Laboratory Study Two will use subjective effects measurement and safety assessments to select the most appropriate dose for use in the clinical trial. The Clinical Trial will then evaluate the efficacy of the final selected dose as a treatment for MA dependence.

The human laboratory study will evaluate the potential efficacy of two doses of EC2 compared to placebo in 15 volunteers. The doses will be selected taking into account safety data obtained in the Phase I study; one will likely be the maximum tolerated dose (MTD) and the other will be a lower dose. This study will use a within-subjects design and will again be conducted under double-blind and placebo controlled conditions. Participants will be randomized to receive placebo and two doses of EC2 in random order. Participants will receive pre-treatment doses of MA (ascending doses of 20 and 30 mg MA IV with a dose of saline placebo interspersed to maintain the blind, dosed at 30 minute intervals). On the 5th day of treatment with the target dose of study medication, these doses of MA will be repeated. On the 6th day of treatment participants will receive a sample dose of 10 mg MA and then will make 4 choices between receiving additional doses of 10 mg MA or a $1 money alternative. This is intended to assess the reinforcing effects of MA compared to those of money. Participants will then be discharged.

Summary of Daily Activities

This section generally pertains to both human laboratory studies, excepting the choice procedures on day 8 which pertain only to the second study. Additional details (e.g. inclusion criteria) are presented following description of the clinical trial, below. After giving informed consent and completing initial screening as outpatients, participants will be admitted for the study. The cardiovascular and subjective effects of MA return to baseline over several hours and are additive with repeated dosing. Continuous HR monitoring and q15 min BP measurements will be started prior to MA dosing and will continue until values have returned to baseline, which will be several hours. Qualified physicians will administer the MA and monitor participants closely until vital signs return to normal. Participants who may demonstrate cardiovascular changes outside of pre-set limits will be dropped from the study. Data on the rewarding effects of MA will be collected prior to and following administration of MA using standard visual-analogue scales (VAS) reflecting ratings of ratings of "High," "Good," "Bad," "Like," "Dislike," "Crave Meth," "Want Meth," and "Desire Meth." Participants will also complete the (ARCI)[46] a validated measure of drug effects. Change from pre-drug baseline will be calculated to reduce variance between participants.

Clinical Trial.

Following at least two weeks of lead-in monitoring to establish baseline MA use, 80 participants will be randomized to receive EC2 or placebo. The dose level of EC2 will be based on findings from Phase I and both EC2 and placebo will be dosed at one capsule PO BID. Participants will return to clinic three times weekly for 12 weeks to provide urine samples for MA testing. Missing samples will be coded as MA-positive. All participants will receive a standard psychosocial treatment once weekly. Contingency management techniques will be used to reinforce clinic attendance. Participants will be encouraged to attend self-help groups and attendance will be noted but there will be no contingencies for not attending. Riboflavin will be used as a marker to monitor treatment adherence. Participants will be followed for 12 weeks after randomization, with one additional follow-up visit after discontinuation of study medication.

Study Procedures

Eligible candidates will proceed to the lead-in phase of the study (weeks −2 to −1) which will establish baseline MA use. Participants will be randomized to receive EC2 or placebo and followed three-times weekly for 12 weeks, with a finial follow-up visit four weeks later.

Inclusion Criteria
1. Be between 21-55 years of age;
2. Be English-speaking volunteers. Those in the human laboratory study must not be seeking treatment at the time of the study whereas those in the clinical trial must be treatment-seeking;
3. Currently using MA and provide at least 2 positive urine tests in two weeks prior to study entry, though participants will not be aware of this requirement;
4. Meet DSM-IV TR criteria for MA dependence; participants may or may not meet criteria for nicotine dependence. Nicotine dependence is allowed;
5. Have the resting pulse must be <95 bpm and resting blood pressure must be <150/95 mmHg.
6. Have hematology and chemistry laboratory tests that are within normal (+/−10%) limits;
7. Have a baseline EKG that is clinically normal;
8. Have an acceptable medical history and brief physical examination in the judgment of the PI.

Exclusion Criteria
1. Meet DSM IV TR criteria for dependence on drugs other than MA or nicotine;
2. Have any history or evidence suggestive of seizure disorder or brain injury;
3. Have any previous medically adverse reaction to MA, including chest pain, or epileptic seizure;
4. Have neurological or psychiatric disorders, such as: psychosis, bipolar illness or major depression; organic brain disease or dementia assessed by clinical interview; history of suicide attempts within the past year and/or current suicidal ideation/plan;
5. Be pregnant or nursing. Other females will either be unable to conceive (i.e., surgically sterilized, sterile, or post-menopausal) or will be using a reliable form of contraception (e.g., abstinence, birth control pills, intra-uterine device, condoms, or spermicide). All females will provide negative pregnancy urine tests before study entry, upon hospital admission, and at the end of study participation;

Stopping Rules—Human Laboratory Study.

Participants will be discharge for inability to comply with study procedures or if they meet discontinuation criteria due to exaggerated response to MA (5 min or more of systolic BP>180 mmHg, diastolic BP>120 mmHg, or heart rate >[(220−age)×0.85]bpm).

Stopping Rules—Clinical Trial.

The clinical trial (phase II) will be halted if the pattern of adverse events indicates that the selected dose of EC2 is inappropriate. The study may be restarted using a different dose.

Motivational Enhancement Therapy

Participants will receive weekly 30-minute substance use counseling based on a standardized, manual-driven psychosocial treatment program incorporating cognitive behavioral therapy and motivational interviewing techniques.

Contingency Management Schedule

Adherence to medications will be measured using weekly pill counts and urine testing for riboflavin. Riboflavin will be added to placebo and active medication capsules (100 mg/dose[47]) to track adherence. Urine samples will be tested using quantitative assessment of fluorescence. This approach has been shown to be sensitive and has been utilized in other pharmacologic trials. The schedule for reinforcing clinic attendance will incorporate an escalating component during the first 3 weeks; payments start at $2 and escalate by $1 per visit until they reach $10. After the first 3 weeks, payment will stabilize at $10 per visit. However, a reset feature is also planned such that payment will revert to the original lowest amount of $2 (and begin escalating again) whenever two or more sessions are missed in a given week. This reset rule will promote compliance with study procedures at least twice weekly, while avoiding an unduly harsh reset penalty for missing a single visit.

Prior to admission, participants in both the human laboratory study and the clinical trial will be interviewed to establish the DSM IV-TR diagnosis for MA abuse. Drug use will be assessed on the type, frequency, and amounts of drugs used, as well as routes of administration. Depression will also be assessed.

Cardiovascular Monitoring.

Beginning 60 minutes before MA administration and at 15 min intervals following MA administration, blood pressure and heart rate will be determined using automatic heart rate and blood pressure assessment. Cardiovascular monitoring will continue for at least 2 h, or until vital signs have returned to baseline.

Morphine-Benzedrine Groups (MGB) Scale of the Addiction Research Center Inventory (ARCI).

This scale reflects stimulant effects. Visual-analogue scales anchored at 0 and 100 will also be used to collect data on effects produced by MA.

Medical History and Physical Exam (Both Studies).

The physician will conduct a standard history and physical exam.

Urine Toxicology.

Standard urine toxicology cups with temperature sensitive strips will be used to collect information on drug use other than MA. Breath alcohol levels will be obtained with a portable Breathalyzer at regular intervals throughout the study.

Clinical Laboratory Assessment.

Blood will be collected in anticoagulant-containing vacutainer tubes for analysis of CBC, chemistry, liver function tests, and renal function tests. A urine-based pregnancy test for females will measure human chorionic gonadotropin.

ECG.

An ECG will be recorded at baseline and will be used to determine eligibility of the participant for the study and several times during the study to document any changes.

Adverse Events.

Participants will be asked on a daily basis if they are experiencing any discomfort or symptoms that might indicate potential side effects of the study drug. Any spontaneously reported symptoms or complaints will be recorded.

Study Medications.

EC2 prepared under good manufacturing practice (GMP) conditions will be provided by SK Life Sciences, South Korea. Placebo capsules will be formulated with lactose. 100 mg riboflavin will be added to both capsules for the outpatient clinical trial. Study medications will be stored in the research pharmacy. The medication will be dosed prior to breakfast and several hours after dinner, without food.

Safety of MA During Treatment with EC2.

EC2 treatment will reduce the effects of MA based on studies conducted in rodents. In the human laboratory study, vital signs and adverse events will be monitored to assess the safety of MA administration during treatment with EC2.

Human Laboratory Study.

Human laboratory study 1 will include 24 participants, of whom 18 will receive EC2 and 4 will receive placebo. This sample size is selected in order to screen for commonly occurring side effects. Human laboratory study 2, with 45 participants divided into three groups of 15 participants may have the power to detect differences in subjective effects ratings of d=1.2 for comparing the impact of treatment with either dose of EC2 to placebo (calculated using G*power).

Clinical Trial.

Study participants will be randomly assigned to EC2 or placebo. Participants will visit the clinic 3 times per week for 12 weeks for a total of 36 clinic visits. The primary outcome will be the MA urinalysis result observed at each clinical visit. Sample size may be estimated using a statistical power analysis algorithm. Sample size considerations may assume that, on average, half of the planned clinical visits (i.e., 18) will be available for analysis and that the within-subject correlation will be at least 0.50. Assuming alpha=0.05 and 0.10 (10%) of the sample in the placebo group are MA negative, a sample size of 33 subjects per group (N=66) may be used to detect a 0.2 unit increase to 0.3 (30%), in the proportion of MA negative urinalyses in the EC2 group with 80% power. Allowing for 20% attrition, this study will plan to enroll N=80 subjects (40 per group).

Data Analysis—Human Laboratory Study.

Descriptive statistics will be used to summarize basic demographic information, drug use variables, and symptom checklist outcomes. The primary outcome measure will be ratings of "High" and scores on the Morphine-Benzedrine Groups (MGB) scale of the Addiction Research Center Inventory (ARCI). Placebo vs. medication groups will be compared using repeated measures ANOVA. Compared to placebo, EC2 treatment will not be associated with increases in the cardiovascular effects of MA or increases in ratings on ratings of "High" following administration of MA. If significant differences between treatment groups are identified, these variables can be included in further analyses as covariates. General linear models for repeated measures will be used to assess placebo vs. medication effects on cardiovascular responses and subjective effects ratings.

Prophetic Example 19

The Compounds of the Method Will Attenuate Various Symptoms of PTSD/ASD in in Multiphase Human Laboratory and Clinical Trials Human subjects will be selected for study based on a diagnosis of PTSD and/or ASD symptoms according to the diagnostic criteria provided in the *Diagnostic and Statistical Manual of Mental Disorders* V (DSM-V). For example, exposure to a traumatic stressor, intrusion symptoms or persistent re-experiencing, avoidance, negative alterations in cognitions and mood, alterations in arousal and reactivity, duration of symptoms for more than 1 month (for PTSD), and significant impairment. Multiphase human laboratory and clinical trials will be designed by adapting Prophetic Examples 15 and 18. Administration of the compounds of the method, e.g., EC2, to the human subjects in need of treatment for PTSD/ASD will commence. The human subjects will be monitored for changes in their expression of certain diagnostic criteria for PTSD/ASD. A statistically significant portion of the human subjects in the experimental group will experience a reduction or cessation of one or more diagnostic criteria, including, for example, aspects of persistent re-experiencing, persistent avoidance and emotional numbing, persistent symptoms of increased arousal not present before, cessation or reduction of symptoms prior to 1 month (avoiding or muting progression of ASD to PTSD), and significant impairment.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

As used herein, "substituted" refers to an organic group as defined below (e.g., an alkyl group) in which one or more bonds to a hydrogen atom contained therein may be replaced by a bond to non-hydrogen or non-carbon atoms. Substituted groups also include groups in which one or more bonds to a carbon(s) or hydrogen(s) atom may be replaced by one or more bonds, including double or triple bonds, to a heteroatom. A substituted group may be substituted with one or more substituents, unless otherwise specified. In some embodiments, a substituted group may be substituted with 1, 2, 3, 4, 5, or 6 substituents. Examples of substituent groups include: halogens (e.g., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; or nitriles. A "per"-substituted compound or group is a compound or group having all or substantially all substitutable positions substituted with the indicated substituent. For example, 1,6-diiodo perfluoro hexane indicates a compound of formula $C_6F_{12}I_2$, where all the substitutable hydrogens have been replaced with fluorine atoms.

Substituted ring groups such as substituted cycloalkyl, aryl, heterocyclyl and heteroaryl groups also include rings and ring systems in which a bond to a hydrogen atom may be replaced with a bond to a carbon atom. Substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some examples, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above and include, without limitation, haloalkyl (e.g., trifluoromethyl), hydroxyalkyl, thioalkyl, aminoalkyl, alkylaminoalkyl, dialkylaminoalkyl, alkoxyalkyl, or carboxyalkyl.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments, the number of ring carbon atoms ranges from 3 to 5, 3 to 6, or 3 to 7. Bi- and tricyclic ring systems include both bridged cycloalkyl groups and fused rings, such as, but not limited to, bicyclo[2.1.1] hexane, adamantyl, or decalinyl. Substituted cycloalkyl groups may be substituted one or more times with non-hydrogen and non-carbon groups as defined above. However, substituted cycloalkyl groups also include rings that may be substituted with straight or branched chain alkyl groups as defined above. Representative substituted cycloalkyl groups may be mono-substituted or substituted more than once, such as, but not limited to, 2,2-, 2,3-, 2,4-, 2,5- or 2,6-disubstituted cyclohexyl groups, which may be substituted with substituents such as those listed above.

Aryl groups may be cyclic aromatic hydrocarbons that do not contain heteroatoms. Aryl groups herein include monocyclic, bicyclic and tricyclic ring systems. Aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups may be phenyl or naphthyl. Although the phrase "aryl groups" may include groups containing fused rings, such as fused aromatic-aliphatic ring systems (e.g., indanyl or tetrahydronaphthyl), "aryl groups" does not include aryl groups that have other groups, such as alkyl or halo groups, bonded to one of the ring members. Rather, groups such as tolyl may be referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl, which may be substituted with substituents such as those above.

Aralkyl groups may be alkyl groups as defined above in which a hydrogen or carbon bond of an alkyl group may be replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Substituted aralkyls may be substituted one or more times with substituents as listed above.

Groups described herein having two or more points of attachment (e.g., divalent, trivalent, or polyvalent) within the compound of the technology may be designated by use of the suffix, "ene." For example, divalent alkyl groups may be alkylene groups, divalent aryl groups may be arylene groups, divalent heteroaryl groups may be heteroarylene groups, and so forth. In particular, certain polymers may be described by use of the suffix "ene" in conjunction with a term describing the polymer repeat unit.

Alkoxy groups may be hydroxyl groups (—OH) in which the bond to the hydrogen atom may be replaced by a bond to a carbon atom of a substituted or unsubstituted alkyl group as defined above. Examples of linear alkoxy groups include, but are not limited to, methoxy, ethoxy, propoxy, butoxy, pentoxy, or hexoxy. Examples of branched alkoxy groups include, but are not limited to, isopropoxy, sec-butoxy, tert-butoxy, isopentoxy, or isohexoxy. Examples of cycloalkoxy groups include, but are not limited to, cyclopropyloxy, cyclobutyloxy, cyclopentyloxy, or cyclohexyloxy. Representative substituted alkoxy groups may be substituted one or more times with substituents such as those listed above.

The term "amine" (or "amino"), as used herein, refers to $NR_5R_6$ groups, wherein $R_5$ and $R_6$ may be independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine may be alkylamino, dialkylamino, arylamino, or alkylarylamino. In other embodiments, the amine may be $NH_2$, methylamino, dimethylamino, ethylamino, diethylamino, propylamino, isopropylamino, phenylamino, or benzylamino. The term "alkylamino" may be defined as $NR_7R_8$, wherein at least one of $R_7$ and $R_8$ may be alkyl and the other may be alkyl or hydrogen. The term "arylamino" may be defined as $NR_9R_{10}$, wherein at least one of $R_9$ and $R_{10}$ may be aryl and the other may be aryl or hydrogen.

The term "halogen" or "halo," as used herein, refers to bromine, chlorine, fluorine, or iodine. In some embodiments, the halogen may be fluorine. In other embodiments, the halogen may be chlorine or bromine.

As used herein, the term "pharmaceutically acceptable" means that the materials (e.g., compositions, carriers, diluents, reagents, salts, and the like) are capable of administration to or upon a mammal with a minimum of undesirable physiological effects such as nausea, dizziness or gastric upset.

Also included in the present invention are pharmaceutically acceptable salts of the compounds of the method, e.g., the Example Compounds. These the compounds of the method, e.g., the Example Compounds, may have one or more sufficiently acidic protons that may react with a suitable organic or inorganic base to form a base addition salt. When it is stated that a compound has a hydrogen atom bonded to an oxygen, nitrogen, or sulfur atom, it is contemplated that the compound also includes salts thereof where this hydrogen atom has been reacted with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of the compounds of the method, e.g., the Example Compounds, may include those formed by the reaction of the compounds of the method, e.g., the Example Compounds, with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). "Pharmaceutically acceptable" means that the cation is suitable for administration to a subject. Examples include $Li^+$, $Na^+$, $K^+$, $Mg^{2+}$, $Ca^{2+}$ and $NR_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is $Li^+$, $Na^+$, $K^+$, $NH_3(C_2H_5OH)^+$ or $N(CH_3)_3(C_2H_5OH)^+$.

Pharmaceutically acceptable salts of the compounds of the method, e.g., the Example Compounds, with a sufficiently basic group, such as an amine, may be formed by reaction of the compounds of the method, e.g., the Example Compounds, with an organic or inorganic acid to form an acid addition salt. Acids commonly employed to form acid addition salts from compounds with basic groups may include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

It will also be understood that certain of the compounds of the method, e.g., the Example Compounds, may be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers may be separated and isolated using any suitable method, such as chromatography.

The various aspects and embodiments disclosed herein are for purposes of illustration and are not intended to be limiting, with the true scope and spirit being indicated by the following claims.

The invention claimed is:

1. A method for treating an alcohol use disorder, comprising:
   providing a subject in need of therapy for an alcohol use disorder; and
   administering to the subject an effective amount of a compound-represented by Formula I:

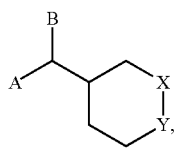

(I)

or a pharmaceutically acceptable salt thereof, wherein:
   X is NR, Y is CH$_2$, A is naphthyl; and B is tetrazolyl; and R is H or a straight or branched-chain C$_1$-C$_4$ alkyl.

2. The method of claim 1, the alcohol use disorder comprising binge drinking of ethanol.

3. The method of claim 1, the compound represented by structural Formula I being characterized by reuptake inhibition percentages at 100 nM for each of human serotonin, human norepinephrine, and human dopamine transporter proteins such that the reuptake inhibition percentages at 100 nM have a subtractive difference at most of less than about 30%.

4. The method of claim 1, the compound represented by structural Formula I being characterized by respective IC$_{50}$ binding concentrations for human serotonin, human norepinephrine, and human dopamine transporter proteins such that one or more of:
   a sum of the respective IC$_{50}$ binding concentrations is less than 131 nM; and
   the respective IC$_{50}$ binding concentrations differ at most by a ratio of less than 4:1.

5. The method of claim 1, the compound being represented by one of the following structural formula:

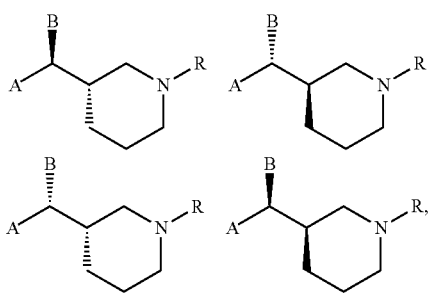

or a pharmaceutically acceptable salt thereof.

6. The method of claim 1, the compound being represented by one of the following structural formulas:

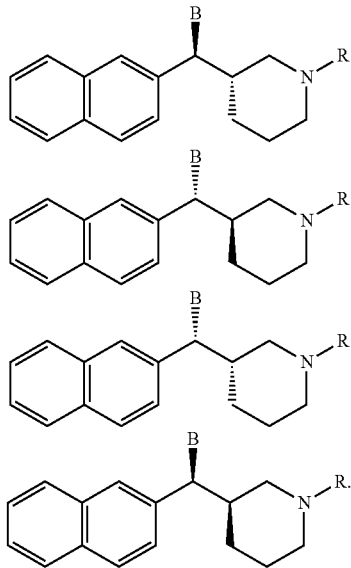

or a pharmaceutically acceptable salt thereof.

7. The method of claim 1, wherein the compound is enantiomerically enriched.

8. The method of claim 1, the compound being selected from the group consisting of:
   (3R)-3-[(R)-naphthalen-2-yl(2H-tetrazol-2-yl)methyl]piperidine;
   (3S)-3-[(S)-naphthalen-2-yl(2H-tetrazol-2-yl)methyl]piperidine;
   (3R)-3-[(S)-naphthalen-2-yl(2H-tetrazol-2-yl)methyl]piperidine;
   (3S)-3-[(R)-naphthalen-2-yl(2H-tetrazol-2-yl)methyl]piperidine;
   (3R)-3-[(R)-naphthalen-2-yl(1H-tetrazol-1-yl)methyl]piperidine;
   (3S)-3-[(S)-naphthalen-2-yl(1H-tetrazol-1-yl)methyl]piperidine;
   (3R)-3-[(S)-naphthalen-2-yl(1H-tetrazol-1-yl)methyl]piperidine;
   (3S)-3-[(R)-naphthalen-2-yl(1H-tetrazol-1-yl)methyl]piperidine;
   (3R)-3-[(R)-naphthalen-1-yl)(2H-tetrazol-2-yl)methyl]piperidine; and
   (3S)-3-[(S)-naphthalen-1-yl)(2H-tetrazol-2-yl)methyl]piperidine.

9. The method of claim 1, the compound being (3S)-3-[(S)-naphthalen-2-yl(2H-tetrazol-2-yl)methyl]piperidine, represented by the following structural formula:

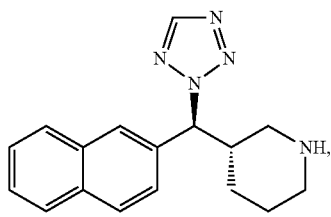 [SMILES: c1ccc2cc([C@H]([C@H]3CCCNC3)n3ncnn3)ccc2c1]

or a pharmaceutically acceptable salt thereof.

* * * * *